(12) United States Patent
Fonnum et al.

(10) Patent No.: US 9,156,925 B2
(45) Date of Patent: Oct. 13, 2015

(54) HYDROPHILIC POLYMERIC PARTICLES AND METHODS FOR MAKING AND USING SAME

(71) Applicants: LIFE TECHNOLOGIES CORPORATION, Carlsbad, CA (US); LIFE TECHNOLOGIES AS, Oslo (NO)

(72) Inventors: Geir Fonnum, Fjellhamar (NO); Grete I. Modahl, Oslo (NO); Nini H. Kjus, Oslo (NO); Astrid E. Molteberg, Fetsund (NO); Diem Tran, Lillestroem (NO); Jo Aaserud, Skjetten (NO); Talha M. Gokmen, Oslo (NO); Steven M. Menchen, Fremont, CA (US); Carl Fuller, Berkeley Heights, NJ (US); Luisa Andruzzi, Beverly, MA (US); Wolfgang Hinz, Killingworth, CT (US)

(73) Assignee: Life Technologies Corporation, Carlsbad, CA (US)

( * ) Notice: Subject to any disclaimer, the term of this patent is extended or adjusted under 35 U.S.C. 154(b) by 173 days.

(21) Appl. No.: 14/082,419

(22) Filed: Nov. 18, 2013

(65) Prior Publication Data

US 2014/0073715 A1 Mar. 13, 2014

Related U.S. Application Data

(63) Continuation of application No. 13/762,941, filed on Feb. 8, 2013.

(60) Provisional application No. 61/731,873, filed on Nov. 30, 2012, provisional application No. 61/719,045, filed on Oct. 26, 2012, provisional application No. 61/597,053, filed on Feb. 9, 2012.

(51) Int. Cl.

| | | |
|---|---|---|
| *C08F 6/24* | (2006.01) | |
| *C08F 8/34* | (2006.01) | |
| *C08F 2/20* | (2006.01) | |
| *C08F 2/26* | (2006.01) | |
| *C07F 7/18* | (2006.01) | |
| *C08F 130/08* | (2006.01) | |
| *C08F 220/58* | (2006.01) | |
| *C08F 230/08* | (2006.01) | |
| *C08F 222/38* | (2006.01) | |
| *C08F 8/32* | (2006.01) | |
| *C12Q 1/68* | (2006.01) | |

(52) U.S. Cl.
CPC . *C08F 8/34* (2013.01); *C07F 7/188* (2013.01); *C07F 7/1852* (2013.01); *C08F 2/20* (2013.01); *C08F 2/26* (2013.01); *C08F 6/24* (2013.01); *C08F 8/32* (2013.01); *C08F 130/08* (2013.01); *C08F 220/58* (2013.01); *C08F 222/385* (2013.01); *C08F 230/08* (2013.01); *C12Q 1/686* (2013.01); *C08F 2800/20* (2013.01); *Y10T 428/2982* (2013.01)

(58) Field of Classification Search
CPC ............ C08F 8/34; C08F 6/24; C08F 130/08; C08F 2/20; C08F 2/26; C08F 220/58; C08F 230/08
USPC ............................ 526/304; 521/149; 524/555
See application file for complete search history.

(56) References Cited

U.S. PATENT DOCUMENTS

| | | | |
|---|---|---|---|
| 4,451,613 A | 5/1984 | Rousseau et al. | |
| 4,507,382 A | 3/1985 | Rousseau et al. | |
| 4,507,497 A | 3/1985 | Reilly, Jr. et al. | |
| 4,511,646 A | 4/1985 | Fohrenkamm et al. | |
| 4,906,715 A | 3/1990 | Mauz et al. | |
| 5,455,143 A | 10/1995 | Ali | |
| 5,677,373 A | 10/1997 | Berge et al. | |
| 7,217,762 B1 | 5/2007 | Jorgedal et al. | |
| 8,574,835 B2 | 11/2013 | Hinz et al. | |
| 2004/0215011 A1 | 10/2004 | Deggerdal et al. | |
| 2005/0014001 A1 | 1/2005 | Fonnum et al. | |
| 2006/0131542 A1 | 6/2006 | Weng et al. | |
| 2006/0205905 A1 | 9/2006 | Inaba et al. | |
| 2007/0299249 A1 | 12/2007 | Songe | |
| 2008/0139399 A1 | 6/2008 | Fonnum et al. | |
| 2009/0069554 A1 | 3/2009 | Finne | |
| 2009/0280182 A1* | 11/2009 | Beck et al. | .............. 424/486 |
| 2009/0291506 A1 | 11/2009 | Fonnum et al. | |
| 2010/0207051 A1 | 8/2010 | Fonnum et al. | |

FOREIGN PATENT DOCUMENTS

| | | |
|---|---|---|
| JP | 02166102 | 6/1990 |
| JP | 2007/217447 | 8/2007 |
| WO | 2010/125170 | 11/2010 |

OTHER PUBLICATIONS

Dufour, B. et al., "A Study of the Hetero Diels-Alder Reaction of N-Alkyl-2-Cyano-1-Azadienes with 2-Vinylindole", *Heterocycles*, vol. 37, No. 3, Oct. 8, 1993, pp. 1455-1458.

Schumann, H. et al., "Synthesis and Characterization of Water-Soluble Tin-Based Metallodendrimers", *Organometallics*. vol. 22, 2003, pp. 2034-2041.

Skinner, W. A. et al., "Effect of Organic Compounds on Reproductive Processes, VI. Alkylating Agents Derived from Various Diamines", *Journal of Medicinal Chemistry*, vol. 10, No. 5, Sep. 1967, pp. 949-950.

* cited by examiner

*Primary Examiner* — Kelechi Egwim

(57) ABSTRACT

A method of forming a particle includes, in a disperse phase within an aqueous suspension, polymerizing a plurality of mer units of a hydrophilic monomer having a hydrophobic protection group, thereby forming a polymeric particle including a plurality of the hydrophobic protection groups. The method further includes converting the polymeric particle to a hydrophilic particle.

8 Claims, 2 Drawing Sheets

HYDROPHILIC POLYMERIC PARTICLES AND METHODS FOR MAKING AND USING SAME

CROSS-REFERENCE TO RELATED APPLICATION(S)

This application is a continuation of U.S. patent application Ser. No. 13/762,941, entitled "Hydrophilic polymeric particles and methods for making and using same," and filed Feb. 8, 2013, which claims benefit of U.S. Provisional Application No. 61/597,053, filed Feb. 9, 2012, claims benefit of U.S. Provisional Application No. 61/719,045, filed Oct. 26, 2012, and claims benefit of U.S. Provisional Application No. 61/731,873, filed Nov. 30, 2012, each of which is incorporated herein by reference in its entirety.

FIELD OF THE DISCLOSURE

This disclosure, in general, relates to hydrophilic polymeric particles and relates to methods for making and using such hydrophilic polymeric particles.

BACKGROUND

Polymeric particles are increasingly being used as components in separation techniques and to assist with detecting analytes in both chemical and biological systems. For example, polymeric particles have been used in chromatographic techniques to separate target molecules from a solution. In another example, polymeric particles having a magnetic coating are utilized in magnetic separation techniques. More recently, polymeric particles have been used to enhance ELISA-type techniques and can be used to capture polynucleotides.

Nevertheless, such separation and analytical techniques have suffered as a result of variance in particle size. Large variance in particle size leads to variance in particle weight, as well as variance in the number of reaction sites available for interacting with target analytes. For magnetic separations techniques, variance in size can lead to low efficiency separations. For chromatographic techniques and various polynucleotide capture techniques, variance in size can lead to variance in the number of sites available for interacting with polynucleotides, leading to variance in capture or separation efficiency.

As such, an improved polymeric particle and method for manufacturing such a polymeric particle would be desirable.

SUMMARY

In a first aspect, a method of forming a particle includes, in a disperse phase within an aqueous suspension, polymerizing a plurality of mer units of a hydrophilic monomer having a hydrophobic protection group, thereby forming a polymeric particle including a plurality of the hydrophobic protection groups, and converting the polymeric particle to a hydrogel particle.

In a second aspect, a method of forming a particle includes, in a disperse phase within an aqueous suspension, polymerizing a plurality of mer units of an acrylamide monomer having a hydrophobic protection group, thereby forming a polymeric particle including a plurality of the hydrophobic protection groups, and converting the polymeric particle to a hydrophilic particle.

In a third aspect, a method of forming a particle includes, in a disperse phase within an aqueous suspension, polymerizing a plurality of mer units of an radically polymerizable monomer with a diacrylamide crosslinker having a hydrophobic protection group, thereby forming a polymeric particle including a plurality of the hydrophobic protection groups. The method further includes removing at least a portion of plurality of the hydrophobic protection groups.

In a fourth aspect, a method of forming a particle includes polymerizing a plurality of mer units of a hydrophilic monomer having a hydrophobic protection group, thereby forming a polymeric particle including a plurality of the hydrophobic protection groups; removing at least a portion of plurality of the hydrophobic protection groups from the polymeric particle to form a hydrophilic particle; and binding an oligonucleotide to the hydrophilic particle In a fifth aspect, a plurality of particles includes at least 100,000 particles. At least one particle of the plurality of particles includes a hydrogel. The plurality of particles has an average particle size of not greater than 100 micrometers and a coefficient of variance of not greater than 5%.

In a sixth aspect, a system includes an array of wells. At least one well of the array of wells is operatively connected with an ISFET sensor. The system further includes a plurality of hydrogel particles having a coefficient of variance of not greater than 5%. At least one of the hydrogel particles of the plurality of hydrogel particles is disposed in a well of the array of wells.

In a seventh aspect, a plurality of particles is formed by the method including, in a disperse phase within an aqueous suspension, polymerizing a plurality of mer units of a hydrophilic monomer having a hydrophobic protection group, thereby forming a polymeric particle including a plurality of the hydrophobic protection groups, and including converting the polymeric particle to a hydrogel particle.

In an eighth aspect, a composition includes an aqueous mixture of an acrylamide monomer and a crosslinker, the acrylamide monomer including a hydrophobic protection group, the monomer and crosslinker included in a mass ratio of monomer:crosslinker in a range of 15:1 to 1:2.

In a ninth aspect, a method of sequencing a polynucleotide includes providing a device including an array of wells. At least one well is operatively connected to an ISFET and includes a particle formed by the method of the above aspects. The particle is attached to a polynucleotide. The method further includes applying a solution including nucleotides of a predetermined type to the device and observing an ionic response to the applying the solution.

In a tenth aspect, a method for nucleotide incorporation includes providing a particle formed by the method of the above aspects. The particle is attached to a nucleic acid duplex including a template nucleic acid hybridized to a primer. The duplex is bound to a polymerase. The method further includes contacting the particle with one or more nucleotides and incorporating at least one nucleotide onto the end of the primer using the polymerase.

In an eleventh aspect, a method of forming a particle includes promoting a seed particle to form a disperse phase in an aqueous suspension, in the disperse phase, polymerizing a plurality of mer units of a hydrophilic monomer having a hydrophobic protection group, thereby forming a polymeric particle including a plurality of hydrophobic protection groups, and converting the polymeric particle to a hydrogel particle.

In a twelfth aspect, a method of forming a particle includes providing a seed particle in an aqueous suspension, the seed particle comprising a hydrophobic polymer, and includes promoting the seed particle to form a disperse phase in the aqueous suspension. The method further includes, in the disperse phase, polymerizing a plurality of mer units of a hydrophilic monomer having a hydrophobic protection group, thereby forming a polymeric particle including a hydrophilic polymer having a plurality of the hydrophobic protection groups. The polymeric particle includes the hydrophobic polymer. The method also includes cleaving the plurality of hydrophobic protection groups from the hydrophilic polymer and extracting the hydrophobic polymer from the polymeric particle to form a hydrogel particle.

In a thirteenth aspect, a particle includes a polymer formed from polymerization of hydroxyalkyl acrylamide and a diacrylamide. The diacrylamide includes a hydroxyl group. The particle absorbs at least 300 wt % water based on the weight of the polymer when exposed to water.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DESCRIPTION OF THE PREFERRED EMBODIMENT(S)

Figure 1:
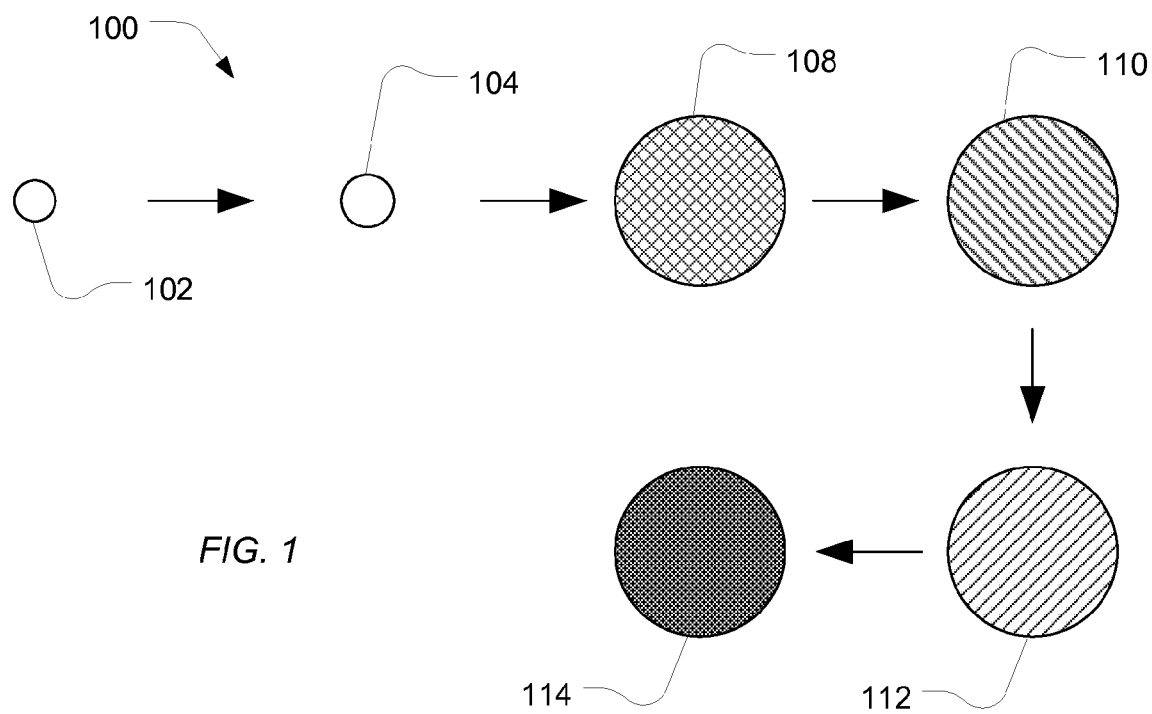
FIG. 1 includes an illustration of an exemplary process flow for manufacturing an exemplary polymeric particle.

In an exemplary embodiment, a method of forming polymeric particles includes polymerizing, in a dispersed phase within an aqueous suspension, a plurality of mer units of a monomer having hydrophilic functional groups protected with a hydrophobic protection group. Polymerizing forms a polymeric particle including a plurality of the hydrophobic protection groups. The method further includes converting the polymeric particle to a hydrophilic particle, such as a hydrogel particle. In an example, the monomer includes a hydrophilic radically polymerizable monomer, such as a hydrophilic vinyl-based monomer, in particular an acrylamide. The monomer is a hydrophilic monomer including hydrophilic functionality protected with a hydrophobic protection group. For example, the hydrophobic protection group can include silyl functionality or derivatives thereof. Polymerizing can also include polymerizing in the presence of a crosslinker, such as a vinyl crosslinker, including exemplary diacrylamide crosslinkers. The crosslinkers can be protected crosslinkers having hydrophobic protection groups. In an example, converting the polymeric particle to a hydrophilic particle can include removing at least a portion of the hydrophobic protection groups from the polymeric particle. In particular, the hydrophobic protection group can be an acid-cleavable protection group, and removing the hydrophobic protection group can include acid cleaving the hydrophobic protection group from the polymeric particle.

Exemplary polymeric particles made by such methods can have a desirable size or coefficient of variance. In particular, the polymeric particles can be hydrophilic. For example, the polymeric particles can include hydrogel particles. Further, the polymeric particles can have an average particle size of not greater than 100 μm, such as not greater than 30 μm, not greater than 3 μm, or not greater than 2 μm. The polymeric particles can have a coefficient of variance not greater than 15%, such as not greater than 5%.

In particular, such particles can be useful in capturing target analytes, such as polynucleotides. In an example, the polymeric particles can be useful in sequencing polynucleotides using sequencing methods that involve light detection or sequencing methods that involve ion detection.

In a particular embodiment, a dispersed phase is formed within an aqueous suspension. The dispersed phase is preferably hydrophobic. In an example, the dispersed phase is formed as a result of promoting seed particles, such as hydrophobic seed particles, to yield the dispersed phase. Promoting facilitates absorption of hydrophobic components in the seed particle.

Monomers having removable hydrophobic protection groups prefer the dispersed phase. The monomers polymerize within the dispersed phase. Optionally, a crosslinker is polymerized with the monomers within the dispersed phase. In an example in which the dispersed phase is formed from a seed particle, such as a hydrophobic seed particle, the polymer associated with the seed particle can be removed. For example, the polymer of the seed particle can be dissolved using solvents and can be extracted from the polymeric particle.

The hydrophobic protection groups can be removed, such as through cleaving at least a portion of the hydrophobic protection groups from the polymeric particle. As a result, a hydrophilic particle is formed, such as a hydrogel particle.

In an example, the resulting in hydrophilic particle can be activated to facilitate conjugation with a target analyte, such as a polynucleotide. For example, cleaving the hydrophobic protection groups can leave a hydrophilic functional group, such as hydroxyl groups, amino groups, thiol groups, or a combination thereof, on the hydrophilic particle. In a particular example, hydroxyl groups can be activated by converting the hydroxyl groups to sulfonate ester groups or chlorine. Sulfonate ester functional groups or chlorine can be substituted or replaced using nucleophilic substitution. In particular, oligonucleotides having a nucleophile terminal group, such as an amine or a thiol group, can be attached to the hydrophilic particle by nucleophilic substitution for the sulfonate groups or chlorine. Such particles can be particularly useful in capturing polynucleotides for use in sequencing techniques.

In another example, the sulfonated particles can be further reacted with mono- or multi-functional mono- or multi-nucleophilic reagents that can form an attachment to the particle while maintaining nucleophilic activity for oligonucleotides comprising electrophilic groups such as maleimide. In addition, the residual nucleophilic activity can be converted to electrophilic activity by attachment to reagents comprising multi-electrophilic groups, which are subsequently to attach to oligonucleotides comprising nucleophilic groups.

Other conjugation techniques include the use of monomers that comprise hydrophobic protecting groups on carboxylic acids during particle synthesis. De-protection of the carboxylic acid group makes available a carboxylic acid group that can be further reacted with oligonucleotides having a nucleophilic group, such as an amine or causing attachment of the oligonucleotide Other conjugation techniques include the use of monomers that comprise hydrophobic protecting groups on amines during particle synthesis. De-protection of the amine group makes available a nucleophilic group that can be further modified with amine reactive bi-functional bis-electrophilic reagents that yield a mono-functional electrophilic group subsequent to attachment to the polymer particle. Such an electrophilic group can be reacted with oligonucleotides having a nucleophilic group, such as an amine or thiol, causing attachment of the oligonucleotide by reaction with the vacant electrophile.

As illustrated in FIG. 1, a method 100 includes providing a seed particle 102. Monomers are added to the suspension and preferably reside in the dispersed phase 104 formed from a promoted seed particle. The monomer and optionally, a crosslinker are polymerized to form a polymeric particle 108. The polymeric particle 108 can be stripped of the seed polymer to form the polymeric particle 110. The hydrophobic protection groups on the polymeric particle 110 are removed to form a hydrophilic particle 112. The hydrophilic particle 112 can be activated to form a conjugated particle 114.

The seed particle 102 can include a seed polymer. In an example, the seed polymer is hydrophobic. In particular, the seed polymer can include a styrenic polymer, an acrylic polymer, an acrylamide, another hydrophobic vinyl polymer, or any combination thereof. In an example, the seed particle 102 is monodisperse, for example, having a coefficient of variance of not greater than 20%. Coefficient of variance (CV) is defined as 100 times the standard deviation divided by the average, where "average" is mean particle diameter and standard deviation is standard deviation in particle size. Alternatively, the "average" can be either the z-average or mode particle diameter. In accordance with usual practice, CV is calculated on the main mode, i.e. the main peak, thereby excluding minor peaks relating to aggregates. Thus some particles below or above mode size may be discounted in the calculation which may, for example, be based on about 90% of total particle number of detectable particles. Such a determination of CV is performable on a CPS disc centrifuge. In particular, a population of seed particles 102 can have a coefficient of variance of not greater than 10%, such as not greater than 5.0%, not greater than 3.5%, not greater than 3%, not greater than 2.5%, not greater than 2%, or even not greater than 1.0%. Further, the seed particle 102 can have an initial particle size of not greater than 0.6 μm. For example, the initial particle size can be not greater than 0.45 μm, such as not greater than 0.35 μm, or even not greater than 0.15 μm. Alternatively, larger seed particles having an initial particle size of at least 3 μm, such as at least 5 μm, at least 10 μm, at least 20 μm, or at least 50 μm, can be used to form larger polymeric particles. In an example, the initial particle size can be not greater than 100 μm.

The seed particle 102 can be promoted within an aqueous suspension to form a promoted dispersed phase 104. In particular, promoting the seed particles includes mixing a solvent and a promoter with the seed particle within the aqueous suspension to form the dispersed phase. Promoted seed particles more readily absorb hydrophobic components. The solvent can be water-miscible. For example, the solvent can include an aldehyde or ketone, such as formaldehyde, acetone, methyl ethyl ketone, diisopropyl ketone, dimethyl formamide, or combinations thereof; an ether solvent, such as tetrahydrofuran, dimethyl ether, or combinations thereof; an ester solvent; a heterocyclic solvent, such as pyridine, dioxane, tetrahydrofurfuryl alcohol, N-methyl-2-pyrrolidone, or combinations thereof; or combinations thereof. In an example, the solvent can include a ketone, such as acetone. In another example, the solvent can include an ether solvent, such as tetrahydrofuran. In an additional example, the solvent can include a heterocyclic solvent, such as pyridine.

The promoter or promoting agent can be hydrophobic and have a low water solubility, such as a water solubility of not greater than 0.01 g/l at 25° C. For example, the promoter can include dioctanoyl peroxide, dioctyladipate, n-butyl phthalate, dodecanol, polystyrene with molecular weight below 20 kD, or a combination thereof. In an example, the dioctanoyl peroxide can also perform as an initiator for a polymerization reaction. The promoter can also be a low molecular weight polystyrene, for example, made in a separate polymerization step using a low monomer/initiator ratio or the addition of chain transfer reagents during the seed polymerization. The promoter is typically emulsified in a high pressure homogenizer.

The aqueous suspension can also include a surfactant. The surfactant can be an ionic surfactant, an amphoteric surfactant, or a non-ionic surfactant. The ionic surfactant can be an anionic surfactant. In another example, the ionic surfactant can be a cationic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate (sodium dodecyl sulfate, (SDS)), or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate; or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof.

An exemplary cationic surfactant includes primary, secondary or tertiary amines, quaternary ammonium surfactants, or any combination thereof. An exemplary quaternary ammonium surfactant includes alkyltrimethylammonium salts such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric surfactant includes a primary, secondary, or tertiary amine or a quaternary ammonium cation with a sulfonate, carboxylate, or phosphate anion. An exemplary sulfonate amphoteric surfactant includes (3-[(3-cholamidopropyl)dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin. In a further example, the surfactant can be a non-ionic surfactant such as a polyethylene glycol-based surfactant.

Returning to FIG. 1, monomers added to suspension preferably naturally reside in the dispersed phase 104 formed from a promoted seed particle. A crosslinker, such as a hydrophobic crosslinker can also be added to the aqueous suspension and preferentially can reside in the dispersed phase. In an example, the crosslinker has a water solubility of not greater than 10 g/l. Further, a porogen can be added to the aqueous suspension and preferentially can reside within the dispersed phase. In a further example, the dispersed phase can include acrydite oligonucleotides, such as an ion-exchanged acrydite oligonucleotide. As illustrated in FIG. 1, the monomer and optionally, the crosslinker are polymerized to form a polymeric particle 108.

The monomer can be a radically polymerizable monomer such as a vinyl-based monomer. In particular, the monomer can include a hydrophilic monomer coupled to a hydrophobic protection group. In an example, the hydrophilic monomer can include acrylamide, vinyl acetate, hydroxyalkylmethacrylate, or any combination thereof. In a particular example, the hydrophilic monomer is an acrylamide, such as an acrylamide including hydroxyl groups, amino groups, carboxyl groups, or a combination thereof. In an example, the hydrophilic monomer is an aminoalkyl acrylamide, an acrylamide functionalized with an amine terminated polypropylene glycol (C, illustrated below), an acrylopiperazine (D, illustrated below), or a combination thereof. In another example, the acrylamide can be a hydroxyalkyl acrylamide, such as hydroxyethyl acrylamide. In particular, the hydroxyalkyl acrylamide can include N-tris(hydroxymethyl)methyl) acrylamide (A, illustrated below), N-(hydroxymethyl)acrylamide (B, illustrated below), or a combination thereof. In a further example, a mixture of monomers, such as a mixture of hydroxyalky acrylamide and amine functionalize acrylamide or a mixture of acrylamide and amine functionalized acrylamide, can be used. In an example, the amine functionalize acrylamide can be included in a ratio of hydroxyalkyl acrylamide:amine functionalized acrylamide or acrylamide:amine functionalized acrylamide in a range of 100:1 to 1:1, such as a range of 100:1 to 2:1, a range of 50:1 to 3:1, a range of 50:1 to 5:1 or even a range of 50:1 to 10:1.

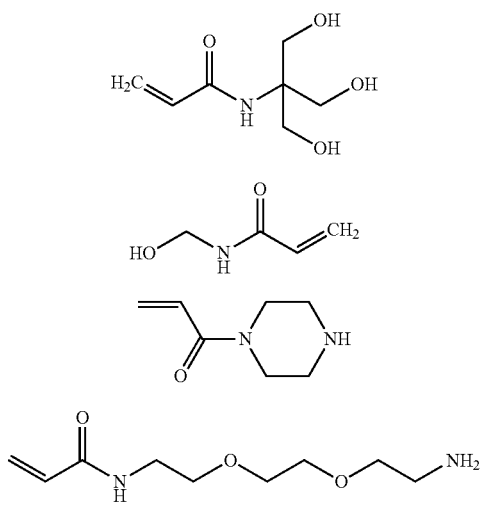

In a particular example, the hydrophilic monomer includes hydroxyl groups or includes amines. The hydrophobic protection group shields the hydrophilicity of the monomer, for example, by bonding to a hydroxyl group or an amine group. Such protection groups are referred to herein as hydroxyl or hydroxy protection groups when bonding to a hydroxyl group. In particular, the hydrophobic protection group is removable, such as through cleaving, for example, acid cleaving. The hydrophobic group can be selected to cleave under acidic conditions that do not result in the hydrolysis of the underlying polymer or portions thereof. For example for pH values lower than 6, when an acrylamide polymer is present, the hydrophobic protection group cleaves at a pH higher than a pH at which the amide portion of the acrylamide hydrolyzes. For pH values higher than 9, the hydrophobic protection group cleaves at a pH lower than a pH at which the amide portion of the acrylamide hydrolyzes.

An exemplary hydrophobic protection group includes an organometallic moiety. For example, the organometallic moiety can form a silyl ether functional group. The silyl ether functional group can be derived from a halogenated silyl compound, such as a compound of the general formulation $R_1Si(R_2)(R_3)(R_4)$, wherein $R_1$ is a halogen, such as chlorine and $R_2$, $R_3$, and $R_4$ are independently selected from hydrogen, alkyl groups such as methyl, ethyl, propyl, butyl, aryl group, silyl groups, ether derivatives thereof, or any combination thereof. An exemplary silyl ether functional group is derived from tert-butyldimethylsilyl chloride, trimethylsilyl chloride, triethylsilyl chloride, tripropylsilyl chloride, tributylsilyl chloride, diphenyl methyl silyl chloride, chloro(dimethyl)phenyl silane, or a combination thereof. In a particular example, the protected monomer includes N-(2-((tert-butyldimethylsilyl)oxy)ethyl)acrylamide or tBDMS-HEAM, N-(2-((triethylsilyl)oxy)ethyl)acrylamide or TES-HEAM, or a combination thereof. In another example, the hydrophobic protection group can include an organic moiety. An exemplary organic moiety can include an alkyloxycarbonyl group moiety, such as t-butyloxycarbonyl, fluorenylmethyloxycarbonyl, or a combination thereof. In an example, such an organic moiety can be a hydrophobic protection group bound to an amine functional group, such as an amine functional group of an amine functionalized acrylamide or copolymer thereof.

The protected monomer can be included in an amount relative to the initial seed polymer, expressed as a ratio of weights (protected monomer:seed polymer), in a range of 100:1 to 1:2, such as a range of 50:1 to 1:1, a range of 45:1 to 2:1, a range of 30:1 to 5:1, or even a range of 20:1 to 8:1. Alternatively, the monomer can be included in an amount in a range of 10:1 to 1:2, such as a range of 5:1 to 1:2, or even a range of 2:1 to 1:2.

The dispersed phase can also include a crosslinker. In an example, the crosslinker is included in a mass ratio of protected monomer to crosslinker in a range of 15:1 to 1:2, such as a range of 10:1 to 1:1, a range of 6:1 to 1:1, or even a range of 4:1 to 1:1. The crosslinker can have a low water solubility (e.g., less than 10 g/l), resulting in a preference for the dispersed phase. In particular, the crosslinker can be a divinyl crosslinker. For example, a divinyl crosslinker can include a diacrylamide, such as N,N'-(ethane-1,2-diyl)bis(2-hydroxyl ethyl)acrylamide, N,N'-(2-hydroxypropane-1,3-diyl)diacrylamide, or a combination thereof. In another example, a divinyl crosslinker includes ethyleneglycol dimethacrylate, divinylbenzene, hexamethylene bisacrylamide, trimethylolpropane trimethacrylate, a protected derivative thereof, or a combination thereof. In a further example, the crosslinker can be protected with a hydrophobic protection group, such as a hydroxyl protection group. In particular, the hydrophobic protection group can be an organometallic moiety. For example, the organometallic moiety can form a silyl ether functional group. An exemplary silyl ether functional group can be derived from tert-butyldimethylsilyl chloride, trimethylsilyl chloride, triethylsilyl chloride, tripropylsilyl chloride, tributylsilyl chloride, diphenyl methyl silyl chloride, chloro(dimethyl)phenylsilane, or a combination thereof. An exemplary protected diacrylamide crosslinker includes N,N'-(ethane-1,2-diyl)bis(N-(2-((tert-butyldimethylsilyl)oxy)ethyl)acrylamide, N,N'-(N-(2-((tert-butyldimethylsilyl)oxy)propane-1,3-diyl)diacrylamide, N,N'-(ethane-1,2-diyl)bis(N-(2-((triethylsilyl)oxy)ethyl)acrylamide, N,N'-(N-(2-((triethylsilyl)oxy)propane-1,3-diyl)diacrylamide, silyl-protected N-[2-(acryloylamino)-1,2-dihydroxyethyl]acrylamide such as N,N'(2,3-bis((triethylsilyl)oxy)butane-1,4-diyl)diacrylamide, or a combination thereof. In another example, the protection group can include an alkyloxycarbonyl group moiety, such as t-butyloxycarbonyl, fluorenylmethyloxycarbonyl, or a combination thereof. In particular, a crosslinker including a hydroxyl group can be protected with a protection group, such as those described above in relation to the protected monomer.

In addition, polymerizing the hydrophilic monomer having a hydrophobic protection can include polymerizing in the presence of a porogen. An exemplary porogen includes an aromatic porogen. In example, the aromatic porogen includes benzene, toluene, xylene, mesitylene, phenethylacetate, diethyladipate, hexylacetate, ethylbenzoate, phenylacetate, butylacetate, or a combination thereof. The porogen typically has a Solubility parameter of 15-20. In another example, the porogen is an alkanol porogen, such as dodecanol. The porogen can be included in amounts relative to the organic phase within the reactive system in a range of 1 wt % to 99 wt %, such as a range of 30 wt % to 90 wt % or even a range of 50 wt % to 85 wt %.

The monomer is chosen from a group of monomers that produce a hydrogel in its unprotected form such that oligonucleotides and polymerases can reach their targets during use.
Hydrophilic acrylamides and especially diacrylamides are difficult to dissolve in a solvent that is not miscible with water and at the same time dissolves a hydrophobic seed polymer. The protection group for both monomer and crosslinker can be chosen such that the solubility of the monomers in a hydrophobic phase is large enough to achieve a concentration large enough to carry out the polymerization. At the same time the protection group may not be so large that polymerization cannot be carried out because of steric hindrance. The deprotection can be performed at conditions that will not hydrolyze the polymer.

Optionally, a polymerization initiator can be included. An exemplary polymerization initiator can initiate polymerization through free radical generation. An exemplary polymerization initiator includes an azo initiator such as oil soluble azo initiators. Another initiator can include ammonium persulfate. A further exemplary initiator can include tetramethylethylenediamine. In an example, the polymerization initiator can be included in an amount of 0.001 wt % to 3 wt % based on the weight of the dispersed phase.

Following polymerization, the polymeric particle 108 can be stripped of the seed polymer to form the polymeric particle 110 still having the hydrophobic protection groups. For example, the seed polymer can be extracted using a solvent, such as an aldehyde or ketone, such as acetone, methyl ethyl ketone, diisopropyl ketone, butylacetate, cyclohexanone, dimethyl formamide, or a combination thereof; a phthalate solvent, such as, n-butyl phthalate; an ether solvent, such as tetrahydrofuran, diisopropyl ether, methyl tertbutyl ether, dimethyl ether, diethyl ether, or a combination thereof; an ester solvent, such as ethyl acetate, butyl acetate, or a combination thereof; a heterocyclic solvent, such as pyridine, dioxane, tetrahydrofurfuryl alcohol, or a combination thereof; halogenated solvents such as dichloro methane, chloroform or a combination thereof. Alternatively, the seed polymer can be extracted following the conversion of the polymeric particle to a hydrophilic particle. For example, the seed polymer can be extracted following deprotecting the polymer of particle, such as removing the silyl groups on the polymer resulting from the protected monomer.

As illustrated in FIG. 1, the polymeric particle 110, once the seed polymer is extracted, can be converted to a hydrophilic polymeric particle by removing at least a portion of the hydrophobic protection groups. For example, the hydrophobic protection groups can be acid-cleaved from the polymeric particles. In particular, such removing can remove substantially all of the hydrophobic protection groups from the polymeric particle, such as removing at least 80% of the hydrophobic protection groups, or even at least 90% of the hydrophobic protection groups.

In an example, the hydrophobic protection groups are acid-cleaved through the addition of an acid, such as an organic acid. In particular, the organic acid can have a pKa in a range of 3.0 to 5.5. For example, the organic acid can include acetic acid, lactic acid, citric acid, or any combination thereof. Alternatively, inorganic acids can be used.

Once at least a portion of the hydrophobic protection groups is removed, a hydrophilic particle 112 is formed. The hydrophilic particle 112 can be a hydrogel particle. A hydrogel is a polymer that can absorb at least 20% of its weight in water, such as at least 45%, at least 65%, at least 85%, at least 100%, at least 300%, at least 1000%, at least 1500% or even at least 2000% of its weight in water.

The hydrophilic polymer 112 can be activated to facilitate conjugation with a target analyte, such as a polynucleotide. For example, functional groups on the hydrophilic particle 112 can be enhanced to permit binding with target analytes or analyte receptors. In a particular example, functional groups of the hydrophilic polymer can be modified with reagents capable of converting the hydrophilic polymer functional groups to reactive moieties that can undergo nucleophilic or electrophilic substitution. For example, hydroxyl groups on the hydrophilic particle 112 can be activated by replacing at least a portion of the hydroxyl groups with a sulfonate group or chlorine. Exemplary sulfonate groups can be derived from tresyl, mesyl, tosyl, or fosyl chloride, or any combination thereof. Sulfonate can act to permit nucleophiles to replace the sulfonate. The sulfonate may further react with liberated chlorine to provide a chlorinated groups that can be used in a process to conjugate the particles. In another example, amine groups on the hydrophilic polymer 112 can be activated.

For example, target analyte or analyte receptors can bind to the hydrophilic polymer through nucleophilic substitution with the sulfonate group. In particular example, target analyte receptors terminated with a nucleophile, such as an amine or a thiol, can undergo nucleophilic substitution to replace the sulfonate groups on the surface of the hydrophilic polymer 112. As a result of the activation, a conjugated particle 114 can be formed.

In another example, the sulfonated particles can be further reacted with mono- or multi-functional mono- or multi-nucleophilic reagents that can form an attachment to the particle while maintaining nucleophilic activity for oligonucleotides comprising electrophilic groups, such as maleimide. In addition, the residual nucleophilic activity can be converted to electrophilic activity by attachment to reagents comprising multi-electrophilic groups, which are subsequently to attach to oligonucleotides comprising nucleophilic groups.

In another example, a monomer containing the functional group can be added during the polymerization. The monomer can include, for example, an acrylamide containing a carboxylic acid, ester, halogen or other amine reactive group. The ester group may be hydrolyzed before the reaction with an amine oligo.

Other conjugation techniques include the use of monomers that comprise hydrophobic protecting groups on amines during particle synthesis. De-protection of the amine group makes available a nucleophilic group that can be further modified with amine reactive bi-functional bis-electrophilic reagents that yield a mono-functional electrophilic group subsequent to attachment to the polymer particle. Such an electrophilic group can be reacted with oligonucleotides having a nucleophilic group, such as an amine or thiol, causing attachment of the oligonucleotide by reaction with the vacant electrophile.

If the particle 112 is prepared from a combination of amino- and hydroxyl-acrylamides, de-protection of the hydrogel particle results in a combination of nucleophilic amino groups and neutral hydroxyl groups. The amino groups can be modified with di-functional bis-electrophilic moieties, such as a di-isocyanate or bis-NHS ester, resulting in a hydrophilic particle reactive to nucleophiles. An exemplary bis-NHS ester includes bis-succinimidyl C2-C12 alkyl esters, such as bis-succinimidyl suberate or bis-succinimidyl glutarate.

Other activation chemistries include incorporating multiple steps to convert a specified functional group to accommodate specific desired linkages. For example, the sulfonate modified hydroxyl group can be converted into a nucleophilic group through several methods. In an example, reaction of the sulfonate with azide anion yields an azide substituted hydrophilic polymer. The azide can be used directly to conjugate to an acetylene substituted biomolecule via "CLICK" chemistry that can be performed with or without copper catalysis. Optionally, the azide can be converted to amine by, for example, catalytic reduction with hydrogen or reduction with an organic phosphine. The resulting amine can then be converted to an electrophilic group with a variety of reagents, such as di-isocyanates, bis-NHS esters, cyanuric chloride, or a combination thereof. In an example, using di-isocyanates yields a urea linkage between the polymer and a linker that results in a residual isocyanate group that is capable of reacting with an amino substituted biomolecule to yield a urea linkage between the linker and the biomolecule. In another example, using bis-NHS esters yields an amide linkage between the polymer and the linker and a residual NHS ester group that is capable of reacting with an amino substituted biomolecule to yield an amide linkage between the linker and the biomolecule. In a further example, using cyanuric chloride yields an amino-triazine linkage between the polymer and the linker and two residual chloro-triazine groups one of which is capable of reacting with an amino substituted biomolecule to yield an amino-triazine linkage between the linker and the biomolecule. Other nucleophilic groups can be incorporated into the particle via sulfonate activation. For example, reaction of sulfonated particles with thiobenzoic acid anion and hydrolysis of the consequent thiobenzoate incorporates a thiol into the particle which can be subsequently reacted with a maleimide substituted biomolecule to yield a thio-succinimide linkage to the biomolecule. Thiol can also be reacted with a bromo-acetyl group.

Alternatively, acrydite oligonucleotides can be used during the polymerization to incorporate oligonucleotides. An exemplary acrydite oligonucleotide can include an ion-exchanged oligonucleotides.

Covalent linkages of biomolecules onto refractory or polymeric substrates can be created using electrophilic moieties on the substrate coupled with nucleophilic moieties on the biomolecule or nucleophilic linkages on the substrate coupled with electrophilic linkages on the biomolecule. Because of the hydrophilic nature of most common biomolecules of interest, the solvent of choice for these couplings is water or water containing some water soluble organic solvent in order to disperse the biomolecule onto the substrate. In particular, polynucleotides are generally coupled to substrates in water systems because of their poly-anionic nature. Because water competes with the nucleophile for the electrophile by hydrolyzing the electrophile to an inactive moiety for conjugation, aqueous systems generally result in low yields of coupled product, where the yield is based on the electrophilic portion of the couple. When high yields of electrophilic portion of the reaction couple are desired, high concentrations of the nucleophile are required to drive the reaction and mitigate hydrolysis, resulting in inefficient use of the nucleophile. In the case of polynucleic acids, the metal counter ion of the phosphate can be replaced with a lipophilic counter-ion, in order to help solubilize the biomolecule in polar, non-reactive, non-aqueous solvents. These solvents can include amides or ureas such as formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, or a combination thereof; carbonates such as dimethyl carbonate, propylene carbonate, or a combination thereof; ethers such as tetrahydrofuran; sulfoxides and sulfones such as dimethylsulfoxide, dimethylsulfone, or a combination thereof; hindered alcohols such as tert-butyl alcohol; or a combination thereof. Lipophilic cations can include tetraalkylammomiun or tetraarylammonium cations such as tetramethylamonium, tetraethylamonium, tetrapropylamonium, tetrabutylamonium, tetrapentylamonium, tetrahexylamonium, tetraheptylamonium, tetraoctylamonium, and alkyl and aryl mixtures thereof, tetraarylphosphonium cations such as tetraphenylphosphonium, tetraalkylarsonium or tetraarylarsonium such as tetraphenylarsonium, and trialkylsulfonium cations such as trimethylsulfonium, or a combination thereof. The conversion of polynucleic acids into organic solvent soluble materials by exchanging metal cations with lipophilic cations can be performed by a variety of standard cation exchange techniques.

In another example, particles can be formed using an emulsion polymerization technique in which a hydrophobic phase forms a dispersed phase within a hydrophilic phase. The monomers, crosslinkers, and other agents and compounds described above that favor hydrophobic phases tend to reside in the hydrophobic phase in which polymerization occurs.

Surfactants, such as those described above can be use in the hydrophilic phase to support emulsion formation. When a seed particle is used, the surfactant can be used at a concentration below the critical micelle concentration. Alternatively, the surfactant can be used at a concentration greater than the critical micelle concentration. Emulsion polymerization is typically performed with a water soluble initiator like potassium or ammonium persulphate.

By adding the intitiator to a heated emulsion of monomers particle nucleation starts in the water phase and the formed particles are stabilized by the surfactants. If most of the particles are created within a short time period, monosized seed particles may be produced. The later increase of particle size happens because the monomer diffuses through the water phase from the large monomer droplets to the much smaller seed particles.

In particular, the above method can produce a plurality of particles having desirable particle size and coefficient of variance. The set of particles can include, for example, 100,000 particles, such as 500,000 particles, greater than 1 million particles, greater than 10 million particles, or even at least $1 \times 10^{10}$. Particles of the plurality of particles may be hydrophilic polymeric particles, such as hydrogel particles. In a particular example, the hydrogel particle can be an acrylamide particle, such as a particle including a crosslinked hydroxyalkyl acrylamide polymer or a crosslinked copolymer of hydroalkyl acrylamide and amine functionalized acrylamide. In another example, the particle can be a crosslinked copolymer of acrylamide and amine functionalized acrylamide.

The plurality of particles can have a desirable particle size, such as a particle size not greater than 100 µm, not greater than 30 µm, or not greater than 3 µm. The average particle size is the mean particle diameter. For example, the average particle size may be not greater than 2 µm, such as not greater than 1.5 µm, not greater than 1.1 µm, not greater than 0.8 µm, not greater than 0.6 µm, not greater than 0.5 µm, or even not greater than 0.3 µm. In a particular example, the average particle size can be in a range of 0.1 µm to 100 µm, such as a range of 0.1 µm to 50 µm or a range of 0.1 µm to 1.1 µm. In some aspects, the above described method provides technical advantages for production of particles having a particle size in a range of 5 µm to 100 µm, such as a range of 20 µm to 100 µm, or a range of 30 µm to 70 µm. In other aspects, the above described method provides technical advantages for the production of particles having a particle size of not greater than 1.1 µm. When the seed is larger, larger particles can be formed. The size of the particles can be adjusted based on the size of the seed particle. Using the present method, the size of the polymeric particle is less dependent on surfactant selection and concentration than when other methods are used.

Further, the plurality of particles is monodisperse and may have a desirably low coefficient of variance, such as a coefficient of variance of not greater than 20%. As above, the coefficient of variance (CV) is defined as 100 times the standard deviation divided by average, where "average" is the mean particle diameter and standard deviation is the standard deviation in particle size. The "average" alternatively can be either the z-average or mode particle diameter. In accordance with usual practice, CV is calculated on the main mode, i.e., the main peak, thereby excluding minor peaks relating to aggregates. Thus, some particles below or above mode size may be discounted in the calculation which may, for example, be based on about 90% of total particle number of detectable particles. Such a determination of CV is performable on a CPS disc centrifuge or a coulter counter. For example, the coefficient of variance (CV) of the plurality of particles may be not greater than 15%, such as not greater than 10%, not greater than 5%, not greater than 4.5%, not greater than 4.0%, not greater than 3.5%, or even not greater than 3.0%. Such CV can be accomplished without filtering or other size exclusion techniques.

In particular, to keep a low variation of the size of the beads, coalescence of droplets should be avoided during the polymerization. This avoidance is easier to achieve in an oil in water emulsion than in a water in oil emulsion since it is easier to stabilize a system where water is the continuous phase. However, hydrophilic monomers do not preferentially reside in an oil phase.

In a further example, a hydrophilic polymeric particle in water can be not greater than 50 wt % polymer, such as not greater than 30 wt % polymer, not greater than 20 wt % polymer, not greater than 10 wt % polymer, not greater than 5 wt % polymer, or even not greater than 2 wt % polymer.

In an additional example, the polymeric particle can have a porosity permitting diffusion of proteins and enzymes. In an example, the polymeric particles can have a porosity to permit diffusion of proteins having a size of at least 50 kilodaltons, such as at least 100 kilodaltons, at least 200 kilodaltons, at least 250 kilodaltons, or even at least 350 kilodaltons.

In another example, when conjugated, the polymeric particle can include a density of polynucleotides, termed nucleotide density, of at least $7 \times 10^4$ per $\mu m^3$. For example, the nucleotide density can be at least $10^5$ per $\mu m^3$, such as at least $10^6$ per $\mu m^3$, at least $5 \times 10^6$ per $\mu m^3$, at least $8 \times 10^6$ per $\mu m^3$, at least $1 \times 10^7$ per $\mu m^3$, or even at least $3 \times 10^7$ per $\mu^3$. In a further example, the nucleotide density can be not greater than $10^{15}$ per $\mu m^3$.

Such polymeric particles can be used in a variety of separations techniques and analytic techniques. In particular, the polymeric particles may be useful in binding polynucleotides. Such binding polynucleotides may be useful in separating polynucleotides from solution or can be used for analytic techniques, such as sequencing. In a particular example illustrated in FIG. 2, such polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques.

In general, the polymeric particle can be treated to include a biomolecule, including nucleosides, nucleotides, nucleic acids (oligonucleotides and polynucleotides), polypeptides, saccharides, polysaccharides, lipids, or derivatives or analogs thereof. For example, a polymeric particle can bind or attach to a biomolecule. A terminal end or any internal portion of a biomolecule can bind or attach to a polymeric particle. A polymeric particle can bind or attach to a biomolecule using linking chemistries. A linking chemistry includes covalent or non-covalent bonds, including an ionic bond, hydrogen bond, affinity bond, dipole-dipole bond, van der Waals bond, and hydrophobic bond. A linking chemistry includes affinity between binding partners, for example between: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement.

In an example, the polymeric particle can be utilized in a system with a surface. The system comprises one or more polymeric particles on a surface. A surface can be a solid surface. A surface can include planar, concave, or convex surfaces, or any combination thereof. A surface can comprise texture or features, including etching, cavitation or bumps. A surface can lack any texture or features. A surface can include the inner walls of a capillary, channel, groove, well or reservoir. A surface can be a mesh. A surface can be porous, semi-porous or non-porous. A surface can be a filter or gel. A surface can include the top of a pin (e.g., pin arrays). The surface may be made from materials such as glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond). A surface can include a solid substrate having a metal film or metal coat. A surface can be optically transparent, minimally reflective, minimally absorptive, or exhibit low fluorescence.

A surface can have dimensions similar to microtiter plates having 96, 384, 1536, 3456 or 9600 wells. A surface can be about 1-20 cm in any one dimension, about 1-10 cm in any one dimension, about 0.10-1 cm in any one dimension, or about 0.001 nm-1 cm in any one dimension. A surface (and any texture or features) can be produced by nanofabrication technologies.

A plurality of polymeric particles can be arranged in a random or ordered array on a surface, or a combination of random and ordered arrays. Ordered arrays include rectilinear and hexagonal patterns. A surface can include a plurality of sites arranged in a random or ordered array, or a combination of both. One or more polymeric particles can be located at one site, some sites or all sites. Some sites can have one polymeric particle and other sites can have multiple polymeric particles. At least one site can lack a polymeric particle. In an array, at least two polymeric particles can contact each other, or have no contact between polymeric particles.

Figure 2:
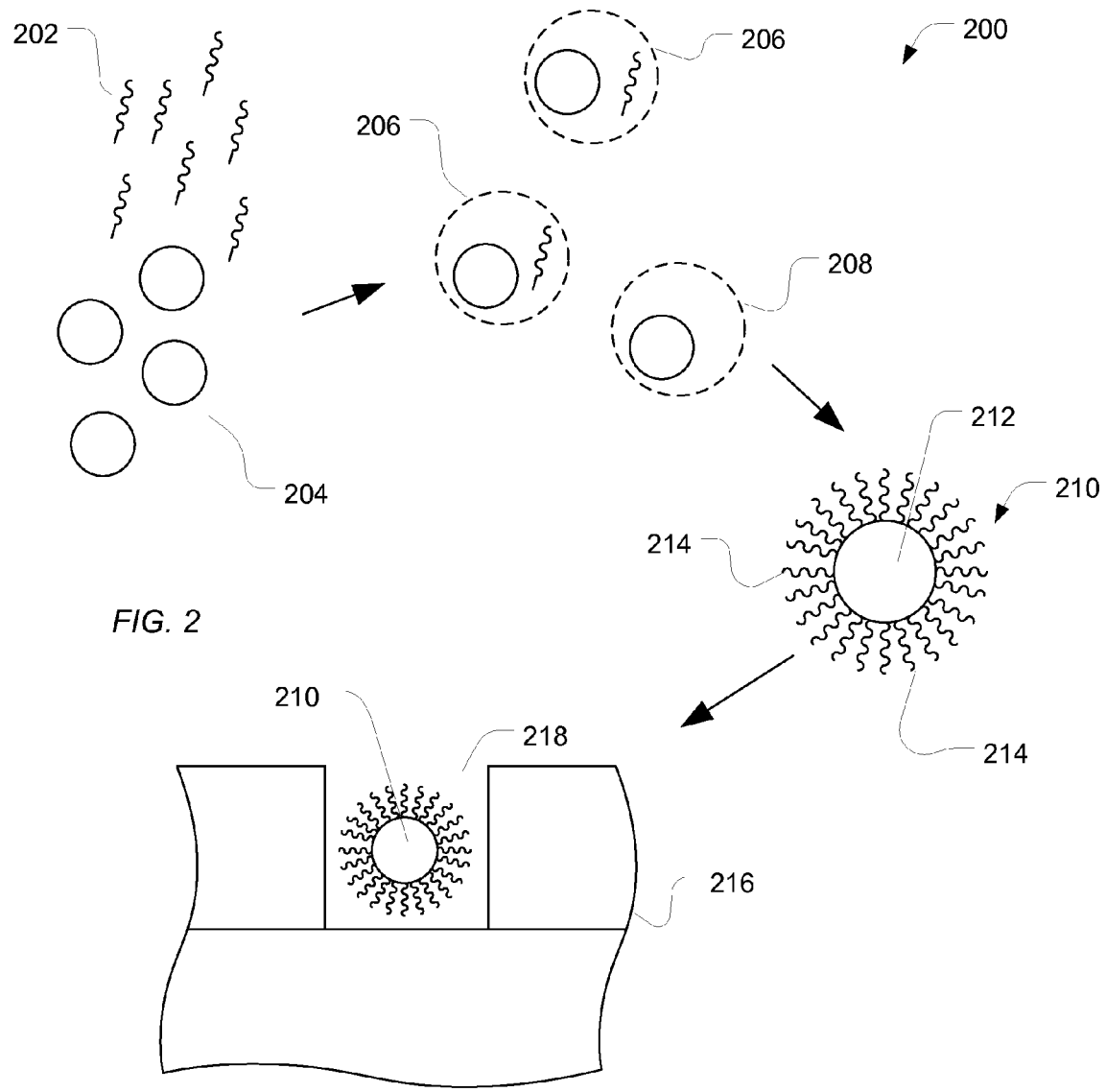
FIG. 2 includes an illustration of an exemplary sequencing method utilizing polymeric particles.

As illustrated in FIG. 2, a plurality of polymeric particles 204 can be placed in a solution along with a plurality of polynucleotides 202. The plurality of particles 204 can be activated or otherwise prepared to bind with the polynucleotides 202. For example, the particles 204 can include an oligonucleotide complementary to a portion of a polynucleotide of the plurality of polynucleotides 202. In another example, the polymeric particles 204 can be modified with target polynucleotides 204 using techniques such as biotin-streptavidin binding.

In a particular embodiment, the hydrophilic particles and polynucleotides are subjected to polymerase chain reaction (PCR) amplification. For example, dispersed phase droplets 206 or 208 are formed as part of an emulsion and can include a hydrophilic particle or a polynucleotide. In an example, the polynucleotides 202 and the hydrophilic particles 204 are provided in low concentrations and ratios relative to each other such that a single polynucleotide 202 is likely to reside within the same dispersed phase droplets as a single hydrophilic particle 204. Other droplets, such as a droplet 208, can include a single hydrophilic particle and no polynucleotide. Each droplet 206 or 208 can include enzymes, nucleotides, salts or other components sufficient to facilitate duplication of the polynucleotide.

In a particular embodiment, an enzyme such as a polymerase is present, bound to, or is in close proximity to the hydrophilic particle or hydrogel particle of the dispersed phase droplet. In an example, a polymerase is present in the dispersed phase droplet to facilitate duplication of the polynucleotide. A variety of nucleic acid polymerase may be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

In an embodiment, the polymerase can be any Family A DNA polymerase (also known as pol I family) or any Family B DNA polymerase. In embodiments, the DNA polymerase can be a recombinant form capable of duplicating polynucleotides with superior accuracy and yield as compared to a non-recombinant DNA polymerase. For example, the polymerase can include a high-fidelity polymerase or thermostable polymerase. In embodiments, conditions for duplication of polynucleotides can include 'Hot Start' conditions, for example Hot Start polymerases, such as Amplitaq Gold® DNA polymerase (Applied Biosciences) or KOD Hot Start DNA polymerase (EMD Biosciences). Typically, a 'Hot Start' polymerase includes a thermostable polymerase and one or more antibodies that inhibit the DNA polymerase and 3'-5' exonuclease activities at ambient temperature.

In embodiments, the polymerase can be an enzyme such as Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*).

In embodiments, the polymerase can be a recombinant form of *Thermococcus kodakaraensis*. In embodiments, the polymerase can be a KOD or KOD-like DNA polymerase such as KOD polymerase (EMD Biosciences), KOD "Hot Start" polymerase (EMD Biosciences), KOD Xtreme Hot Start DNA Polymerase (EMD Biosciences), KOD XL DNA polymerase (EMD Biosciences), Platinum® Taq DNA Polymerase (Invitrogen), Platinum® Taq DNA Polymerase High Fidelity (Invitrogen), Platinum® Pfx (Invitrogen), Accuprime™ Pfx (Invitrogen), Accuprime™ Taq DNA Polymerase High Fidelity (Invitrogen) or Amplitaq Gold® DNA Polymerase (Applied Biosystems). In embodiments, the polymerase can be a DNA polymerase containing analogous mutations to those polymerases discussed herein.

In embodiments, duplication of the polynucleotide can include modulating the duplication conditions. Modulating can optionally include: increasing or decreasing the polymerase concentration; increasing or decreasing the nucleotide concentration; increasing or decreasing a cation concentration; increasing or decreasing a reaction temperature, time or pH, or the like. The modulating can include increasing or decreasing the rate of the reaction, increasing or decreasing the yield of product of the reaction, or the like. In embodiments, duplication can be performed in the presence of appropriate buffers or nucleotides (including nucleotide analogs or biotinylated nucleotides).

In particular, the polynucleotide to be amplified can be captured by the polymeric particle. Exemplary methods for capturing nucleic acid can include: hybridizing a polynucleotide to an oligonucleotide that is attached to a polymeric particle. In embodiments, methods for capturing nucleic acids comprise: (a) providing a polymeric particle attached to a single-stranded oligonucleotide (e.g., a capture oligonucleotide); (b) providing a single-stranded polynucleotide; and (c) hybridizing the single-stranded oligonucleotide to the single-stranded polynucleotides, thereby capturing the single-stranded polynucleotide to the polymeric particle. In embodiments, each of the polymeric particles can be attached with a plurality of single-stranded oligonucleotides (e.g., capture oligonucleotides). In embodiments, step (c) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide.

In an example, the method further includes amplifying the polynucleotide into a plurality of polynucleotides and attaching at least a portion of the plurality of polynucleotides to the hydrophilic particle, thereby generating a hydrophilic particle including a plurality of attached polynucleotides. Alternatively, the method can further include amplifying the polynucleotide into a plurality of complementary polynucleotides by extending the oligonucleotide, thereby generating a hydrogel particle including a plurality of attached polynucleotides.

In embodiments, methods for nucleotide incorporation comprise: conducting a nucleotide polymerization reaction on a polynucleotide that is hybridized to an oligonucleotide that is attached to a polymeric particle. In embodiments, methods for nucleotide incorporation comprise: (a) providing a polymeric particle attached to a single-stranded oligonucleotide (e.g., a primer oligonucleotide); (b) providing a single-stranded template polynucleotide; (c) hybridizing the single-stranded oligonucleotide to the single-stranded template polynucleotide; and (d) contacting the single-stranded template polynucleotide with a polymerase and at least one nucleotide under conditions suitable for the polymerase to catalyze polymerization of at least one nucleotide onto the single-stranded oligonucleotide, thereby conducting nucleotide incorporation. In embodiments, each of the polymeric particles can be attached with a plurality of single-stranded oligonucleotides (e.g., capture oligonucleotides). In embodiments, steps (b), (c) or (d) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, a system comprises a single-stranded polynucleotide hybridized to a single-stranded oligonucleotide which is attached to a polymeric particle, wherein at least one nucleotide is polymerized onto the end of the single-stranded oligonucleotide.

In embodiments, methods for primer extension comprise: conducting a primer extension reaction on a polynucleotide that is hybridized to an oligonucleotide that is attached to a polymeric particle. In embodiments, methods for nucleic acid primer extension comprise: (a) providing a polymeric particle attached to a single-stranded oligonucleotide (e.g., a primer oligonucleotide); (b) providing a single-stranded template polynucleotide; (c) hybridizing the single-stranded oligonucleotide to the single-stranded template polynucleotide; and (d) contacting the single-stranded template polynucleotide with a polymerase and at least one nucleotide under conditions suitable for the polymerase to catalyze polymerization of at least one nucleotide onto the single-stranded oligonucleotide, thereby extending the primer. In embodiments, each of the polymeric particles can be attached with a plurality of single-stranded oligonucleotides (e.g., capture oligonucleotides). In embodiments, step (b), (c) or (d) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, a system comprises a single-stranded polynucleotide hybridized to a single-stranded oligonucleotide which is attached to a polymeric particle, wherein the single-stranded oligonucleotide is extended with one or more nucleotides.

In embodiments, methods for nucleic acid amplification comprise: conducting a primer extension reaction on a polynucleotide that is hybridized to an oligonucleotide which is attached to a polymeric particle. In embodiments, methods for nucleic acid amplification comprise: (a) providing a polymeric particle attached to a single-stranded oligonucleotide (e.g., a primer oligonucleotide); (b) providing a single-stranded template polynucleotide; (c) hybridizing the single-stranded oligonucleotide to the single-stranded template polynucleotide; (d) contacting the single-stranded template polynucleotide with a polymerase and at least one nucleotide under conditions suitable for the polymerase to catalyze polymerization of at least one nucleotide onto the single-stranded oligonucleotide so as to generate an extended single-stranded oligonucleotide. In embodiments, the method further comprises: (e) removing (e.g., denaturing) the single-stranded template polynucleotide from the extended single-stranded oligonucleotide so that the single-stranded oligonucleotide remains attached to the polymeric particle; (f) hybridizing the remaining single-stranded oligonucleotide to a second single-stranded template polynucleotide; and (g) contacting the second single-stranded template polynucleotide with a second polymerase and a second at least one nucleotide, under conditions suitable for the second polymerase to catalyze polymerization of the second at least one nucleotide onto the single-stranded oligonucleotide so as to generate a subsequent extended single-stranded oligonucleotide. In embodiments, steps (e), (f) and (g) can be repeated at least once. In embodiments, the polymerase and the second polymerase comprise a thermostable polymerase. In embodiments, the conditions suitable for nucleotide polymerization include conducting the nucleotide polymerization steps (e.g., steps (d) or (g)) at an elevated temperature. In embodiments, the conditions suitable for nucleotide polymerization include conducting the nucleotide polymerization step (e.g., steps (d) or (g)) at alternating temperatures (e.g., an elevated temperature and a relatively lower temperature). In embodiments, the alternating temperature ranges from 60-95° C. In embodiments, the temperature cycles can be about 10 seconds to about 5 minutes, or about 10 minutes, or about 15 minutes, or longer. In embodiments, methods for nucleic acid amplification can generate one or more polymeric particles each attached to a plurality of template polynucleotides comprising sequences that are complementary to the single-stranded template polynucleotide or to the second single-stranded template polynucleotide. In embodiments, each of the polymeric particles can be attached with a plurality of single-stranded oligonucleotides (e.g., capture oligonucleotides). In embodiments, step (b), (c), (d), (e), (f) or (g) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, methods for nucleic acid amplification (as described above) can be conducted in an aqueous phase solution in an oil phase (e.g., dispersed phase droplet).

Following PCR, particles are formed, such as particle 210, which can include the hydrophilic particle 212 and a plurality of copies 214 of the polynucleotide. While the polynucleotides 214 are illustrated as being on a surface of the particle 210, the polynucleotides can extend within the particle 210. Hydrogel and hydrophilic particles having a low concentration of polymer relative to water can include polynucleotide segments on the interior of and throughout the particle 210 or polynucleotides can reside in pores and other openings. In particular, the particle 210 can permit diffusion of enzymes, nucleotides, primers and reaction products used to monitor the reaction. A high number of polynucleotides per particle produces a better signal.

In embodiments, polymeric particles from an emulsion-breaking procedure can be collected and washed in preparation for sequencing. Collection can be conducted by contacting biotin moieties (e.g., linked to amplified polynucleotide templates which are attached to the polymeric particles) with avidin moieties, and separation away from polymeric particles lacking biotinylated templates. Collected polymeric particles that carry double-stranded template polynucleotides can be denatured to yield single-stranded template polynucleotides for sequencing. Denaturation steps can include treatment with base (e.g., NaOH), formamide, or pyrrolidone.

In an exemplary embodiment, the particle 210 can be utilized in a sequencing device. For example, a sequencing device 216 can include an array of wells 218. A particle 210 can be placed within a well 218.

In an example, a primer can be added to the wells 218 or the particle 210 can be pre-exposed to the primer prior to placement in the well 218. In particular, the particle 210 can include bound primer. The primer and polynucleotide form a nucleic acid duplex including the polynucleotide (e.g., a template nucleic acid) hybridized to the primer. The nucleic acid duplex is an at least partially double-stranded polynucleotide. Enzymes and nucleotides can be provided to the well 218 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 216 and can migrate to the well 218. Excitation energy can be also provided to the well 218. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 218 can change. Such a change in pH can be detected by ion sensitive field effect transistors (ISFET). As such, a change in pH can be used to generate a signal indicating the order of nucleotides complementary to the polynucleotide of the particle 210.

In particular, a sequencing system can include a well, or a plurality of wells, disposed over a sensor pad of an ionic sensor, such as a field effect transistor (FET). In embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In embodiments, an FET can be a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In embodiments, one or more microfluidic structures can be fabricated above the FET sensor array to provide for containment or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

Returning to FIG. 2, in another example, a well 218 of the array of wells can be operatively connected to measuring devices. For example, for fluorescent emission methods, a well 218 can be operatively coupled to a light detection device. In the case of ionic detection, the lower surface of the well 218 may be disposed over a sensor pad of an ionic sensor, such as a field effect transistor.

One exemplary system involving sequencing via detection of ionic byproducts of nucleotide incorporation is the Ion Torrent PGM™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ sequencer detects the nucleotide incorporations by detecting the hydrogen ion byproducts of the nucleotide incorporations. The Ion Torrent PGM™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ sequencer can be found, for example, in U.S. patent application Ser. No. 12/002,781, now published as U.S. Patent Publication No. 2009/0026082 and issued U.S. Pat. No. 8,262,900; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

Embodiments of the polymeric particles exhibit technical advantages when used in sequencing techniques, particularly ion-based sequencing techniques. In particular, embodiments of the polymeric particles are non-buffering or enhance read lengths or accuracy.

In a further example, the polymeric particles can exhibit greater uniformity and lower CV without filtering than particles made through other methods. For example, the above methods can directly form the polymer particles without applying any kind of selection process such as filtering or using a centrifuge. In particular, emulsion polymerization can be used to produce particles suitable for seed particles. Typically seed particles are non-crosslinked to be able to adsorb the promoter molecule.

Normally styrene is used to produce seed particles with a CV of less than 5%, and reports of other monomers is limited. Unexpectedly and advantageously, tBDMS HEAM can be used to produce seeds with a CV of 2% using a method, such as the emulsion polymerization method, described above.

Further, embodiments of the present method provide for size control based on the size of the seed particle. Additionally, embodiments of particles made by such methods provide an increase in conjugation, such as a 60% to 80% increase in conjugation, over other methods.

For example, when measured on an Ion Torrent 314 PGM, embodiments of conjugated polymeric particles exhibit Q17 mean read lengths of at least 200 bp, such as at least 250 bp, at least 300 bp, at least 350 bp, or even at least 400 bp. In particular, conjugated polymeric particles can exhibit Q17 mean read lengths of at least 500 bp. In another example, populations of conjugated polymeric particles exhibit a 200Q17 run of at least 200K, such as at least 300K, at least 350K, or even at least 400K.

EXAMPLES

Example 1

A silyl protected acrylamide monomer, (N-(2-((tert-butyldimethylsilyl)oxy)ethyl)acrylamide), is formed from a hydroxyalkylacrylamide monomer and a halogenated silyl group.

t-Butyldimethylsilyl chloride (66.11 g, 439 mmol) is added in three portions at 30 min intervals to a solution of hydroxyethylacrylamide (50.01 g, 434 mmol) and imidazole (73.94 g, 1086 mmol) in DMF (132 g) at 0° C. under an inert atmosphere (Ar). Extra DMF (18.90 g) is added 15 minutes after the last addition. The reaction mixture is allowed to gradually reach room temperature and is stirred for approximately 24 hours. The reaction mixture is quenched with water (101 g) and stirred for one hour. The mixture is then extracted with diethyl ether and washed with water and brine. The organic phase is dried ($MgSO_4$ over night. Evaporation gives 93.59 g product. 4-methoxyphenol (MEHQ) (9 mg, 100 ppm) is added towards the end of the evaporation. The product is stored at −20° C.

Example 2

A silyl protected acrylamide monomer, (N-(2-((tert-butyldimethylsilyl)oxy)ethyl)acrylamide) (tBDMS-HEAM), is polymerized in a dispersed phase and is deprotected to form a hydrogel particle.

An initiator emulsion is formed by mixing 1.14 g sodium dodecyl sulfate (SDS), 190 g water, 9.50 g acetone, and 19.0 g dioctanoylperoxide with an ultraturax type Ystral™ X10/25 homogeniser ("ultraturax") for 2 minutes and is homogenized with a pressure homogenizer for 7 minutes.

In a 0.5 L flask, 202.42 g of a 0.53 micron monodisperse polystyrene seed dispersion with 7.2 w % solids content is mixed with 115.65 g of the initiator emulsion. The mixture is stirred at 26° C. for 20 hours giving a promoted seed solution.

A PVP solution is formed from 16.02 g polyvinylpyrrolidone (PVP) K-30. K-30 is slowly added to 959 g water and stirred for 30 minutes, followed by addition of 1.08 g SDS.

A buffer solution is prepared from 47.99 g sodium hydrogen carbonate added to 912 g water.

A monomer emulsion is prepared from 19.63 g toluene, 11.49 g tBDMS-HEAM, 0.77 g ethylene glycol dimethacrylate (EDMA), 187.42 g water and 186.4 g PVP solution mixed by ultraturax for 2 minutes, and further homogenized for 5 minutes.

In a 0.5 L reactor, 29.45 g of the promoted seed particles and 189.93 g of the monomer emulsion is added, followed by 26.65 g buffer solution. The mixture is stirred for 2 hours at 25° C. and then 53.33 g water is added. The mixture is heated to 60° C. After 1 hour at 60° C., the temperature is raised to 70° C. and maintained at 70° C. for 5 hours.

The reaction mixture is transferred to a 1 liter centrifugation flask and centrifuged in a Sorvall RC3CPlus centrifuge for 60 minutes at 4500 RPM. The creamy flotation product is transferred to a new 1 liter flask and is centrifuge twice in tetrahydrofuran (THF).

The THF swollen gel sediment is mixed with glacial acetic acid and water to a weight ratio of 1:3:1 and shaken at room temperature over night. The gel is worked by removing the supernatant after centrifugation and adding a mixture of THF and water in a ratio THF:water 1:1, two times and water once, followed by three times with dimethylformamide (DMF) and three times with dry DMF.

Example 3

A silyl protected acrylamide monomer, (N-(2-((tert-butyldimethylsilyl)oxy)ethyl)acrylamide) (tBDMS-HEAM), is polymerized in a dispersed phase formed from polystyrene particles and is deprotected to form a hydrogel particle.

A carbonate buffer solution is prepared from 42.1 g sodium hydrogen carbonate added to 800 g water to give a 0.5 M buffer solution. The pH of the buffer is adjusted to 10 with 0.5 M sodium hydroxide.

An initiator emulsion is prepared from 0.96 g SDS, 160 g water, 8.00 g acetone, and 16.0 g dioctanoylperoxide. The pH is adjusted to 9 with 0.5 M carbonate buffer solution. The mixture is homogenized with an ultraturax type Ystral™ X10/25 homogeniser ("ultraturax") for 2 minutes and homogenized with a pressure homogenizer for 6 minutes.

In a 0.5 L flask, 31.2 g of 0.31 micron monodisperse polystyrene seed dispersion with 15.91 w % solids content is mixed with 103.1 g of the initiator emulsion. The mixture is stirred at 26° C. for 20 hours, giving a promoted seed dispersion.

A PVA solution is prepared by slowly adding 80 g of 87-89% hydrolyzed polyvinylalcohol (PVA) to 2000 g water, stirring and heating to 80° C. for 1 hour and cooling. An amount of 91 g of the PVA solution is mixed with 867 g water, 0.74 g SDS and 4.24 g 0.5 M sodium carbonate buffer.

The monomer emulsion is prepared from 29.2 g toluene, 7.71 g tBDMS-HEAM, 0.76 g EDMA, and 249 g PVA solution mixed by ultraturax for 2 minutes, and further homogenized for 5 minutes.

In a 0.5 L reactor, 13.3 g of the promoted seed particles and 287 g of the monomer emulsion is added. The mixture is stirred for 1 hour at 25° C. and is heated to 50° C. After 1 hour at 50° C., the temperature is raised to 70° C. After two hours, 2.8 ml of 0.5 M buffer solution is added, and the temperature is maintained for one more hour.

The reaction mixture is transferred to a 1 liter centrifugation flask and centrifuged in a Sorvall RC3CPlus centrifuge for 60 minutes at 4500 RPM. The creamy flotation product is transferred to a new 1 liter flask and is centrifuged twice in THF.

To 102 g of the THF swollen gel sediment, glacial acetic acid and water is added in a weight ratio of 1:3:1 and the dispersion is shaken at room temperature over night. The gel is worked by removing the supernatant after centrifugation and adding THF and water in a ratio of THF:water 1:1 twice, followed by three centrifugations with DMF and three centrifugation with dry DMF.

The solids content of the product is determined to be 0.48 g and the diameter of the bead in water was determined to be 1.6 micron by microscopy.

Example 4

Hydrogel particles formed in accordance with Example 3 are activated using tresyl chloride.

In particular, 26 g of the DMF dispersion containing 3.08% hydroxyl gel from Example 3 above is washed three times with 30 ml anhydrous DMF by centrifugation and removing the supernatant. After the last centrifugation, the volume of the gel in DMF is adjusted to 26 mL and the tube is shortly flushed with argon. An amount of 0.241 ml of anhydrous pyridine is added, followed by 0.318 g tresyl chloride. The tube is shaken over night. The dispersion is centrifuged with 30 ml ice cold anhydrous DMF four times, removing the supernatant after each centrifugation, and is centrifuged two times with ice cold anhydrous N-methyl-2-pyrrolidone (NMP). The particles are re-suspend in 50 mL (2% dry) of anhydrous NMP.

Example 5

Hydrogel particles formed in accordance with Example 3 are activated using fosyl chloride.

An amount of 26 g of DMF dispersion containing 3.08% hydroxyl gel from Example 3 is washed three times with 30 ml anhydrous DMF by centrifugation and removing the supernatant. After the last centrifugation, the volume of the gel in DMF is adjusted to 26 mL and the tube is shortly flushed with argon. An amount of 0.080 ml anhydrous pyridine is added, followed by 0.113 g fosyl chloride. The tube is shaken over night and centrifuged, removing the supernatant and adding 30 ml of ice cold anhydrous DMF four times and ice cold anhydrous NMP twice. The particles are re-suspend in 50 mL (2% dry) of anhydrous NMP.

Example 6

Hydrogel particles formed in accordance with Example 3 are activated using mesyl chloride.

An amount of 16 g of DMF containing 3.08% hydroxyl gel from Example 3 is washed three times with 30 ml anhydrous DMF by centrifugation and removing the supernatant. After the last centrifugation, the volume of the gel in DMF is adjusted to 16 mL and the tube is shortly flushed with argon. An amount of 0.049 ml anhydrous pyridine is added, followed by 0.121 g mesyl chloride. The tube is shaken over night and centrifuged, removing the supernatant and adding 30 ml of ice cold anhydrous DMF four times and ice cold anhydrous NMP twice. The particles are re-suspend in 50 mL (2% dry) of anhydrous NMP.

Example 7

A silyl protected acrylamide monomer, (N-(2-((tert-butyldimethylsilyl)oxy)ethyl)acrylamide) (tBDMS-HEAM), is polymerized with divinyl benzene crosslinker in a dispersed phase formed from polystyrene particles and is deprotected to form a hydrogel particle.

An initiator emulsion is prepared from 1.26 g SDS, 210 g water, 10.5 g acetone and 21.0 g dioctanoylperoxide mixed with an ultraturax type Ystral™ X10/25 homogeniser ("ultraturax") for 2 minutes and homogenized with a pressure homogenizer for 7 minutes.

In a 0.5 L flask, 40.7 g of 0.31 micron monodisperse polystyrene seed dispersion with 15.9 w % solids content is mixed with 142.2 g of the initiator emulsion. The mixture is stirred at 26° C. for 48 hours, giving a promoted seed dispersion.

A PVA solution is prepared by slowly adding 80 g polyvinylalcohol (PVA) to 2000 g water and stirring and heating to 80° C. for 1 hour. The PVA solution is subsequently cooled.

To 208 g of the concentrated PVA solution is added 1806 g water, 1.76 g SDS and 7.68 g borax, forming a PVA borax solution.

Amounts of 31.08 g toluene, 9.79 g tBDMS HEAM, 0.37 g 80% divinylbenzene (DVB) (comprising 0.296 g DVB and 0.074 g ethylvinylbenzene), 273.7 g PVA borax solution are mixed by ultraturax for 2 minutes, and further homogenized for 5 minutes to form a monomer emulsion.

In a 0.5 L reactor, 10.1 g of the promoted seed particles is mixed with 289.9 g of the monomer emulsion. The mixture is stirred for 1 hour at 30° C., 1 hour at 50° C., and 2 hours at 75° C.

The reaction mixture is transferred to a 1 liter centrifugation flask and centrifuged in a Sorvall RC3CPlus centrifuge for 80 minutes at 4500 RPM. The creamy flotation product is collected and centrifuged six times in THF.

To 160 g of the THF swollen gel sediment is added glacial acetic acid and water in a weight ratio of 1:3:1. The dispersion is shaken at room temperature over night. The gel is worked by removing the supernatant after centrifugation and adding THF and water in a ratio of THF:water 1:1 two times and water once, followed by three times with DMF. The solids content of the DMF is then determined to be 1.01 g. The bead dispersion was transferred to water and inspected by microscopy. The beads were monosized and the bead diameter is 1.9 micron.

Example 8

A silyl protected acrylamide monomer, (N-(2-((tert-butyldimethylsilyl)oxy)ethyl)acrylamide) (tBDMS-HEAM), is polymerized with a protected crosslinker in a dispersed phase formed from polystyrene particles and is deprotected to form a hydrogel particle.

A concentrated PVA solution is prepared from 80 g polyvinylalcohol (PVA) slowly added to 2000 g water. The solution is stirred and heated to 80° C. for 1 hour and is cooled.

To 160.5 g of the concentrated PVA solution, 1425 g water, 1.56 g SDS and 6.06 g borax are added. The pH of the solution is adjusted to 8.2 with 2M HCl.

Amounts of 11.8 g toluene, 11.80 g 3-phenylpropanol, 0.15 g 2,2'-azobis-(2-methylbutyronitrile) (AMBN), 7.78 g tBDMS HEAM, 1.44 g N,N'-(N-(2-((triethylsilyl)oxy)propane-1,3-diyl)diacrylamide) (TES-PBAM) (82% purity) and 291.6 g PVA borax solution are mixed by ultraturax for 2 minutes, and further homogenized for 5 minutes to form a monomer emulsion.

In a 0.5 L reactor, 5.96 g of a water dispersion of polystyrene seed particles (seed diameter 0.385 μm, 8.08 weight % solids) is mixed with 294.5 g of the monomer emulsion. Argon gas (10-20 ml/min) is bubbled through the mixture, while stirring and heating 1 hours at 30° C. and 1 hour at 50° C. The argon flow is stopped, and heating and stirring continued for 3 hours at 80° C.

The reaction mixture is transferred to a 1 liter centrifugation flask and centrifuged in a Sorvall RC3CPlus centrifuge for 50 minutes at 4500 RPM. The creamy flotation product is collected and centrifuged four times in THF.

To 209 g of the THF swollen gel sediment is added glacial acetic acid 209 g and water 105 g. The mixture is shaken at room temperature overnight. The gel is worked up by removing the supernatant after centrifugation and adding THF and water in a ratio of THF:water 1:1 two times and water once, followed by three times with DMF.

The solids content of the dispersion is determined to be 1.97 g. The diameter of a water swollen gel can be measured in a microscope with phase contrast equipment to 1.9 μm. The CV is not greater than 5.0%.

Example 9

A silyl protected acrylamide monomer, (N-(2-((tert-butyldimethylsilyl)oxy)ethyl)acrylamide) (tBDMS-HEAM), is polymerized with a N,N'-(ethane-1,2-diyl)bis(N-((tert-butyldimethylsilyl)oxy)ethyl)acrylamide (tBDMS EBHEAM) crosslinker in a dispersed phase formed from polystyrene particles and is deprotected to form a hydrogel particle.

A concentrated PVA solution is formed from 80 g polyvinylalcohol (PVA) slowly added to 2000 g water, followed by stirring and heating to 80° C. for 1 hour and cooling.

To 88 g of the concentrated PVA solution, 785 g water, 0.88 g SDS, and 3.33 g borax are added to from a PVA borax solution.

A monomer emulsion is formed from 7.82 g toluene, 0.040 g 2,2'-azobis-(2-methylbutyronitrile) (AMBN), 2.06 g tBDMS HEAM, 0.51 g tBDMS-EBHEAM (95 purity) and 92.9 g PVA borax solution mixed by ultraturax for 2 minutes, and further homogenized for 5 minutes.

In a 0.5 L reactor, 1.65 g of a water dispersion of seed particles (seed diameter 0.319 μm, 8.07 weight % solids) is mixed with 88.34 g of the monomer emulsion. Argon gas (10-20 ml/min) is bubbled through the mixture while stirring and heating 1 hour at 30° C. and 2 hours at 40° C. The argon flow is stopped, and heating and stirring continued for 3 hours at 80° C.

The reaction mixture is transferred to a 1 liter centrifugation flask and centrifuged in a Sorvall RC3CPlus centrifuge for 50 minutes at 4500 RPM. The creamy flotation product is collected and is centrifuged twice in THF.

To 83.9 g of the THF swollen gel sediment, the same weight of glacial acetic acid and half the weight of water is added. The mixture is shaken at room temperature overnight. The gel is worked by removing the supernatant after centrifugation and adding THF and water in a ratio of THF:water 1:1 two times and water once, followed by three times with DMF.

The solids content of the dispersion is determined to be 1.63 g. The diameter of a water swollen gel can be measured in a microscope with phase contrast equipment and is on average 1.6 μm. The CV is not greater than 5.0%.

Example 10

A silyl protected acrylamide monomer, (N-(2-((tert-butyldimethylsilyl)oxy)ethyl)acrylamide) (tBDMS-HEAM), is polymerized with a divinyl benzene (DVB) crosslinker in a dispersed phase formed from polystyrene particles and is deprotected to form a hydrogel particle.

An initiator emulsion is prepared from 1.2 g SDS, 200 g water, 10 g acetone and 20.0 g dioctanoylperoxide mixed with an ultraturax type Ystral™ X10/25 homogeniser ("ultraturax") for 2 minutes and homogenized with a pressure homogenizer for 7 minutes.

In a 0.5 L flask, 31.64 g of 0.13 micron monodisperse polystyrene seed dispersion with 4.55 w % solids content is mixed with 15.84 g of the initiator emulsion. The mixture is stirred at 26° C. for 6 days, giving a promoted seed dispersion.

A borax solution is prepared with 1922 g water mixed with 5.92 g SDS and 7.33 g borax.

A monomer emulsion is prepared from 172.4 g toluene, 54.76 g tBDMS HEAM, 2.75 g 80% divinylbenzene (DVB) (comprising 2.2 g DVB and 0.55 g ethylvinylbenzene) and 1468 g of the borax solution mixed by ultraturax and further homogenized for 17 minutes.

In a 0.5 L reactor, 22.6 g of the promoted seed particles is mixed with 277.6 g of the monomer emulsion. The mixture is stirred for 1 hour at 30° C., 1 hour at 40° C. and 2 hours at 75° C.

The reaction mixture is transferred to a 1 liter centrifugation flask and centrifuged in a Sorvall RC3CPlus centrifuge for 90 minutes at 4500 RPM. The creamy flotation product is collected and is centrifuged four times in THF.

To 73.3 g of THF swollen gel sediment, an equal weight of glacial acetic acid and 36.7 g water are added, and the dispersion is shaken at room temperature over night. The gel is worked by removing the supernatant after centrifugation and adding THF and water in ratios THF:water 7:3 and THF:water 6:4; followed by three centrifugations with DMF.

The solids content of the dispersion is determined to be 1.50 g.

Example 11

A silyl protected acrylamide monomer, (N-(2-((tert-butyldimethylsilyl)oxy)ethyl)acrylamide) (tBDMS-HEAM), is polymerized with a DVB crosslinker in a dispersed phase formed from polystyrene particles and is deprotected to form a hydrophilic particle.

A concentrated PVA solution is prepared from 80 g polyvinylalcohol (PVA) slowly added to 2000 g water. The dispersion is stirred and is heated to 80° C. for 1 hour and cooled.

To 208 g of the concentrated PVA solution, 1814 g water, 2.08 g SDS and 7.71 g borax is added to form a PVA borax solution.

A monomer emulsion is prepared from 22.34 g toluene, 0.164 g 2,2'-azobis-(2-methylbutyronitrile) (AMBN), 16.58 g tBDMS HEAM, 3.46 g 80% divinylbenzene (comprising 2.77 g DVB and 0.69 g ethylvinylbenzene) and 275 g PVA borax solution mixed by ultraturax for 2 minutes, and further homogenized for 5 minutes.

In a 0.5 L reactor, 8.46 g of a water dispersion of seed particles (seed diameter 0.550 μm, 7.20 weight % solids) is mixed with 292.15 g of the monomer emulsion. The mixture is stirred and heated for 1 hour at 30° C., 1 hour at 50° C. and 2 hours at 75° C.

The reaction mixture is transferred to a 1 liter centrifugation flask and centrifuged in a Sorvall RC3CPlus centrifuge for 50 minutes at 4500 RPM. The creamy flotation product is collected and is centrifuged twice in THF.

To 83.9 g of the THF swollen gel sediment, the same weight of glacial acetic acid and half the weight of water are added. The mixture is shaken at room temperature overnight. The gel is worked by removing the supernatant after centrifugation and adding THF and water in a ratio of THF:water 1:1 two times and water once, followed by three times with DMF.

The solids content of the DMF is 7.5 g. The diameter of a water swollen gel can be measured in a microscope with phase contrast equipment and is determined to be 1.8 µm on average. The CV is not greater than 5.0%.

Example 12

A silyl protected acrylamide monomer, (N-(2-((tert-butyldimethylsilyl)oxy)ethyl)acrylamide) (tBDMS-HEAM), is polymerized with a tBDMS-EBHEAM crosslinker in a dispersed phase formed from polystyrene particles and is deprotected to form a hydrogel particle.

A concentrated PVA solution is formed from 80 g polyvinylalcohol (PVA) slowly added to 2000 g water, followed by stirring and heating to 80° C. for 1 hour and cooling.

To 88 g of the concentrated PVA solution, 785 g water, 0.88 g SDS, and 3.33 g borax is added to form a PVA borax solution.

A monomer emulsion is formed from 7.82 g toluene, 0.040 g 2,2'-azobis-(2-methylbutyronitrile) (AMBN), 2.06 g tBDMS HEAM, 0.96 g tBDMS-EBHEAM (95 purity) and 92.9 g PVA borax solution mixed by ultraturax for 2 minutes, and further homogenized for 5 minutes.

In a 0.5 L reactor, 1.65 g of a water dispersion of seed particles (seed diameter 0.319 µm, 8.07 weight % solids) is mixed with 88.34 g of the monomer emulsion. Argon gas (10-20 ml/min) is bubbled through the mixture while stirring and heating 1 hour at 30° C. and 2 hours at 40° C. The argon flow is stopped, and heating and stirring continued for 3 hours at 80° C.

The reaction mixture is transferred to a 1 liter centrifugation flask and centrifuged in a Sorvall RC3CPlus centrifuge for 50 minutes at 4500 RPM. The creamy flotation product is collected and is centrifuged twice in THF.

To 83.9 g of the THF swollen gel sediment, the same weight of glacial acetic acid and half the weight of water is added. The mixture is shaken at room temperature over night. The gel is worked by removing the supernatant after centrifugation and adding THF and water in a ratio of THF:water 1:1 two times and water once, followed by three times with DMF.

The solids content of the dispersion is determined to be 1.63 g. The diameter of a water swollen gel can be measured in a microscope with phase contrast equipment and is on average 1.6 µm. The CV is not greater than 5.0%.

Example 13

A silyl protected acrylamide monomer, (N-(2-((tert-butyldimethylsilyl)oxy)ethyl)acrylamide) (tBDMS-HEAM), is polymerized with N,N'-(ethane-1,2-diyl)bis(N-((tert-butyldimethylsilyl)oxy)ethyl)acrylamide) (TBDMS EBHEAM) as crosslinker in a dispersed phase formed from polystyrene particles and is deprotected to form a hydrophilic particle.

A concentrated PVA solution is prepared by adding 80 g polyvinylalcohol (PVA) slowly to 2000 g water while stirring. The mixture is stirred and is heated to 80° C. for 1 hour and cooled.

To 241.8 g of the concentrated PVA solution, 2129.6 g water, 2.32 g SDS and 9.97 g borax are added to form a PVA borax solution.

A monomer emulsion is prepared by mixing 72.68 g toluene, 0.29 g 2,2'-azobis-(2-methylbutyronitrile) (AMBN), 14.59 g tBDMS HEAM, 4.46 g TBDMS EBHEAM and 835.8 g PVA borax solution, mixed by ultraturax for 2 minutes, and further homogenized for 9 minutes in a high pressure Gauline APV-100 homogenizer at 400 Bar.

In a 1 L reactor, 16.86 g of a water dispersion of seed particles (seed diameter 0.319 µm, 8.07 weight % solids) is mixed with 897 g of the monomer emulsion. The mixture is stirred and heated for 3 hour at 40° C. while bubbling argon through the mixture at 0.05 l/min for the first 2 hours and at 0.15 L/min for 1 hour. The argon flow is then stopped and the emulsion is heated for 3 hours at 80° C.

The reaction mixture is transferred to a 1 liter centrifugation flask and centrifuged in a Sorvall RC3CPlus centrifuge for 60 minutes at 4700 RPM. The creamy flotation product is transferred to a new 500 mL glass flask and resuspended to 370.74 g with water, the pH is adjusted to 3.86 with 21.09 g 0.5 M acetic acid. The mixture is stirred at 60° C. for 2 hours.

The gel is worked up by adding 9 volumes of THF to the deprotected gel, and centrifuged in a Sorvall RC3CPlus centrifuge for 10 minutes at 3500 RPM, followed by two centrifugations with DMF and two centrifugations with dry DMF, all with addition of 7.5% THF prior to centrifugation. The solids content of the gel in DMF is determined to be 6.37 g. The bead dispersion is transferred to water and inspected by microscopy and the bead diameter is 1.7 micron in water.

Example 14

Hydrogel particles formed in accordance with Example 13 are activated using methanesulfonyl chloride.

1.51 g of hydroxyl gel from Example 13 dispersed in DMF is divided into two centrifugation bottles and washed three times by centrifugation and removing the supernatant using a solvent mix of 200 ml of anhydrous DMF and 15 g anhydrous THF. After the last centrifugation, the content of the two bottles are pooled together and washed once more with anhydrous DMF. The dry content is determined to be 2.32 weight %.

54.74 g of the DMF dispersion containing 2.32 w % hydroxyl gel from above is transferred to a three necked round bottom boiling flask with mechanical stirring, before 8.76 g of DMF is added to adjust the dry content to 2.00%. The round bottom boiling flask is flushed continuously with argon. An amount of 0.2077 g of anhydrous pyridine is added, followed by 0.1692 g methanesulfonyl chloride. The flask is stirred at room temperature over night.

The dispersion is centrifuged with 200 ml anhydrous DMF three times, removing the supernatant after each centrifugation, and is re-suspended in anhydrous N-methyl-2-pyrrolidone (NMP) to 122.81 g suspension. The dry content is determined to be 0.91%, giving 1.12 g of activated gel particles.

Example 15

Approximately 280 million hydrogel particles are prepared as disclosed in Example 11 and subjected to conditions to facilitate duplication of polynucleotides present in the disperse phase droplets.

The hydrogel particles are incubated in the presence of a DNA library (L499, approximately 70 million molecules) and Amplitaq Gold® DNA Polymerase (Applied Biosystems) or KOD Hot Start DNA Polymerase (EMD Biosciences). The sample is applied to an Ion OneTouch™ System (Life Technologies), templated and enriched essentially according to the manufacturer's instructions. Percentage recovery of hydrogel particles prior to enrichment is determined using a Guava SYBR Gold Stain system. Enrichment of the hydrogel particles is performed using an Ion OneTouch ES™ System (Life Technologies), essentially according to the manufacturer's instructions (Life Technologies). Post-recovery percentages for hydrogel particles (Table 1) are found to be lower when using a KOD polymerase; however, the total post-enrichment recovery percentages are greater when using a KOD polymerase (27.4%) as compared to 9.5% and 18.2%, respectively for Amplitaq Gold® DNA polymerase.

TABLE 1

| Enzyme | No. of Particles In (M) | No. of Particles Recovered Post 1T (M) | Post-1T Recovery (%) | No. of Particles Recovered Post-ES (M) | Post-ES Recovery (%) |
|---|---|---|---|---|---|
| Amplitaq | 280 | 218 | 90.0 | 24.1 | 9.5 |
| KOD | 280 | 153 | 54.7 | 42.0 | 27.4 |

Example 14

Polymeric particles are prepared in accordance with Example 9, sulfonated to provide 15% mesylation, and treated with acetate and concentrated ammonia. Following conjugation and PCR, the polymeric particles are utilized in a sequencing test using the Ion Torrent 316 chip.

The polymeric particles exhibit a 200q17 value of 1.2M, such as at least 1.4 million. Further, the polymeric particles exhibit an aq17 base test of at least 350M, such as at least 400M. In addition, the particles exhibit a q17 mean of at least of 175, such as at least 180.

Example 15

A silyl protected acrylamide monomer, (N-(2-((tert-butyldimethylsilyl)oxy)ethyl)acrylamide) (tBDMS-HEAM), is polymerized with a tBDMS-EBHEAM crosslinker in a dispersed phase formed from polystyrene particles and is deprotected to form a hydrogel particle.

An emulsion is prepared by first dissolving 1.74 g SDS in 290.00 g water and then adding 14.50 g acetone and 29.00 g bis(2-ethylhexyl) adipate (DOA). The emulsion is mixed by ultraturax for 2 minutes, and further homogenized for 5.6 minutes in a high pressure Gauline APV-100 homogenizer at 400 Bar.

31.14 g of this emulsion is added to 43.89 g of seed particles (seed diameter 0.140 μm, 4.85 weight % solids) in a flask. The mixture is shaken at 40° C. for 40 h in a shaking bath for activation.

An SDS borax solution is prepared by dissolving 4.54 g SDS and 9.69 g borax to 2369.8 g water.

A monomer emulsion is formed from 125.29 g 2-phenethyl acetate, 0.468 g 2,2'-azobis-(2-methylbutyronitrile) (AMBN), 19.51 g tBDMS HEAM, 5.99 g tBDMS-EBHEAM and 816.75 g SDS borax solution mixed by ultraturax for 5 minutes, and further homogenized for 9.68 minutes.

In a 1 L reactor, 62.53 g of a water dispersion of activated seed particles is mixed with 938.1 g of the monomer emulsion. The mixture is stirred and heated at 40° C. for 2 h. The mixture is further stirred and heated at 40° C. for another hour while argon gas (150-200 ml/min) is bubbled through the mixture. The amount of $O_2$ in the emulsion at this point is measure to be 0 ppb. The argon flow is stopped, and heating and stirring continued for 10 hours at 70° C.

The reaction mixture is transferred to four 250 mL centrifugation flasks and centrifuged in a Beckman Coulter Avanti J-20 XP centrifuge for 60 minutes at 13000 RPM. The supernatants are discarded and the sediments are collected and transferred into a glass flask by adding water.

pH of the aqueous dispersion of gels is adjusted to 3.8 by adding 0.5 M acetic acid solution. The acidified gel dispersion is shaken at 60° C. in a shaking bath for 2 h and cooled.

The gel dispersion is transferred into three 1 L flasks, 300 g THF is added to each, the flasks are shaken at room temperature for 30 min on a shaking table and centrifuged in a Thermo Scientific Thermo Scientific Sorvall RC3CPlus centrifuge for 25 minutes at 4500 RPM. The upper phases of resulting biphasic mixtures are discarded, 50 g THF is added to each flask, the flasks are shaken at room temperature for 30 min on a shaking table and centrifuged for 25 minutes at 4500 RPM. Supernatants are discarded.

Contents of each flask are divided into two 250 mL centrifuge flasks. Approximately 100 g DMF is added on each flask and the flasks are shaken overnight at room temperature on a shaking table. Contents of each flask are totaled to 200 g by adding 20 g THF and an amount of DMF. The flasks are centrifuged in a Beckman Coulter Avanti J-20 XP centrifuge for 70 minutes at 13000 RPM. Supernatants are discarded.

Approximately 100 g DMF is added on each flask and the flasks are shaken for 40 min at room temperature on a shaking table. Contents of each flask are totaled to 200 g by adding 20 g THF and an amount of DMF. The flasks are centrifuged in a Beckman Coulter Avanti J-20 XP centrifuge for 70 minutes at 13000 RPM. Supernatants are discarded and all the sediments are combined into a new flask by using minimal amounts of DMF.

The solids content of the dispersion is determined to be 2.34 g. The diameter of a water swollen gel is measured in a microscope with phase contrast equipment and is on average 0.80 μm.

Water swollen gel is further analyzed in a disc centrifuge instrument (CPS Instruments, Inc, model DC20000) using a gradient of 3 and 7 w % sucrose solutions and a rotation speed of 15000 RPM. The diameter is measured as 0.4995 μm using a particle density of 1,032 g/ml. CV (number) is measured as 3.6%.

Example 16

A silyl protected acrylamide monomer, (N-(2-((tert-butyldimethylsilyl)oxy)ethyl)acrylamide) (tBDMS-HEAM), is polymerized with a tBDMS-EBHEAM crosslinker in a dispersed phase formed from polystyrene particles and is deprotected to form a hydrogel particle.

An emulsion is prepared by first dissolving 1.98 g SDS in 330.05 g water and then adding 16.51 g acetone and 33.00 g DOA. The emulsion is mixed by ultraturax for 2 minutes, and further homogenized for 6.4 minutes in a high pressure Gauline APV-100 homogenizer at 400 Bar.

37.71 g of this emulsion is added to 68.57 g of seed particles (seed diameter 0.081 μm, 4.91 weight % solids) in a flask. The mixture is shaken at 40° C. for 20 h in a shaking bath for activation.

An SDS borax solution is prepared by dissolving 3.77 g SDS and 7.59 g borax to 1975.6 g water.

A monomer emulsion is formed from 33.89 g 2-phenethyl acetate, 0.126 g 2,2'-azobis-(2-methylbutyronitrile) (AMBN), 5.26 g tBDMS HEAM, 1.61 g tBDMS-EBHEAM and 223.32 g SDS borax solution mixed by ultraturax for 5 minutes, and further homogenized for 2.6 minutes.

In a 250 mL reactor, 20.31 g of a water dispersion of activated seed particles is mixed with 228.23 g of the monomer emulsion. The mixture is stirred and heated at 40° C. for 2 h. The mixture is further stirred and heated at 40° C. for another hour while argon gas (150-200 ml/min) is bubbled through the mixture. The amount of $O_2$ in the emulsion at this point is measure to be 230 ppb. The argon flow is stopped, and heating and stirring continued for 10 hours at 70° C.

The reaction mixture is transferred to a 250 mL centrifugation flask and centrifuged in a Beckman Coulter Avanti J-20 XP centrifuge for 90 minutes at 12500 RPM. The supernatant is discarded and the sediment is collected and transferred into a glass flask by adding water.

pH of the aqueous dispersion of gels is adjusted to 3.85 by adding 0.5 M acetic acid solution. The acidified gel dispersion is shaken at 60° C. in a shaking bath for 2.5 h and cooled.

The gel dispersion is transferred into a 1 L flask, 170.06 g THF is added, the flask is shaken at room temperature for 10 min on a shaking table and centrifuged in a Thermo Scientific Thermo Scientific Sorvall RC3CPlus centrifuge for 30 minutes at 4500 RPM. The upper phase of resulting biphasic mixture is discarded. 86.81 g THF is added, the flask is shaken at room temperature for 15 min on a shaking table and centrifuged for 30 minutes at 4500 RPM. Supernatant is discarded.

200 g DMF is added on the gel sediment in 1 L flask and this suspension is divided in two 250 mL centrifuge flasks. The flasks are shaken at room temperature for 153 min on a shaking table and contents of each flask are totaled to 200 g by adding 30 g THF and an amount of DMF. The flasks are centrifuged in a Beckman Coulter Avanti J-20 XP centrifuge for 90 minutes at 14000 RPM. Supernatants are discarded.

100 g DMF is added to each flask and the suspensions are shaken at room temperature for 20 min on a shaking table. Contents of each flask are totaled to 200 g by adding 30 g THF and an amount of DMF and the flasks are centrifuged in a Beckman Coulter Avanti J-20 XP centrifuge for 90 minutes at 14000 RPM. Supernatants are discarded and all the sediments are combined into a new flask by using minimal amounts of DMF. The solids content of the dispersion is determined to be 2.03 g.

Water swollen gel is further analyzed in a disc centrifuge instrument (CPS Instruments, Inc, model DC20000) using a gradient of 3 and 7 w % sucrose solutions and a rotation speed of 20000 RPM. The diameter is measured as 0.2885 µm using a particle density of 1.032 g/ml. CV (number) is measured as 5.56%.

Example 17

A protected amino acrylamide monomer (N-tert-butoxycarbonyl-N'-acryloyl-piperazine) and is polymerized with tBDMS-HEAM monomer and tBDMS-EBHEAM crosslinker in a dispersed phase formed from polystyrene particles and is deprotected to form an amino hydrogel particle.

An emulsion is prepared by first dissolving 1.74 g SDS in 290.00 g water and then adding 14.50 g acetone and 29.00 g DOA. The emulsion is mixed by ultraturax for 2 minutes, and further homogenized for 5.6 minutes in a high pressure Gauline APV-100 homogenizer at 400 Bar.

41.33 g of this emulsion is added to 62.93 g of seed particles (seed diameter 0.126 µm, 4.59 weight % solids) in a flask. The mixture is shaken at 40° C. for 40 h in a shaking bath for activation.

An SDS borax solution is prepared by dissolving 4.54 g SDS and 9.69 g borax to 2369.8 g water.

A monomer emulsion is formed from 34.22 g 2-phenethyl acetate, 0.13 g AMBN, 4.98 g tBDMS HEAM, 1.61 g tBDMS-EBHEAM, 0.37 g N-tert-butoxycarbonyl-N'-acryloyl-piperazine and 221.73 g SDS borax solution mixed by ultraturax for 5 minutes, and further homogenized for 4 minutes.

In a 250 mL reactor, 17.09 g of a water dispersion of activated seed particles is mixed with 233.1 g of the monomer emulsion. The mixture is stirred and heated at 40° C. for 2 h. The mixture is further stirred and heated at 40° C. for another hour while argon gas (150-200 ml/min) is bubbled through the mixture. The amount of $O_2$ in the emulsion at this point is measure to be 500 ppb. The argon flow is stopped, and heating and stirring continued for 10 hours at 70° C.

The reaction mixture is transferred to a 250 mL centrifugation flask and centrifuged in a Beckman Coulter Avanti J-20 XP centrifuge for 60 minutes at 12000 RPM. The supernatant is discarded and the sediment is collected and transferred into a glass flask by adding water.

pH of the aqueous dispersion of gels is adjusted to 3.8 by adding 0.5 M acetic acid solution. The acidified gel dispersion is shaken at 60° C. in a shaking bath for 2.5 h and cooled.

The gel dispersion is transferred into a 1 L flask, 317.24 g THF is added, the flask is shaken at room temperature for 30 min on a shaking table and centrifuged in a Thermo Scientific Thermo Scientific Sorvall RC3CPlus centrifuge for 30 minutes at 4500 RPM. The upper phase of resulting biphasic mixture is discarded. 169.63 g THF is added, the flask is shaken at room temperature for 23 min on a shaking table and the flask is centrifuged for 30 minutes at 4500 RPM. Supernatant is discarded.

Approximately 170 g water is added on the gel sediment and the flask is shaken at room temperature overnight on a shaking table. The flask is centrifuged for 30 minutes at 4500 RPM. Supernatant is discarded.

Approximately 170 g water is added on the gel sediment.

32.2 g of a suspension of the hydrogel (1.55 weight % solids) is diluted with 33 g of water. The pH is adjusted to pH 1.0 with 3.2 mL 2M HCl. The suspension is transferred to a 250 mL reactor along with 54 g water. The suspension is heated at 60° C. for 18 hours. The reaction mixture is then transferred to a 250 mL centrifuge flask in a Beckman Coulter Avanti J-20 XP.

The gel is worked up by centrifugation after first diluting with water and titrating the suspension to ca pH 10 with 10 weight % NaOH, giving a total weight of 175 g. After repeating this, the gel is worked up further three times with water. Centrifugation speed is gradually reduced from 14500 rpm to 6000 rpm for 5 minutes during this process. After discarding the supernatant the gel is then diluted with DMF to 175 g, and the obtained suspension is shaken over night. After centrifuging at 6500 rpm for 5 minutes and discarding the supernatant, workup is continued with three more corresponding washings with DMF.

The gel is diluted to NMP to 175 g and centrifuged at 7000 rpm for 5 minutes. The dry substance is then adjusted to 0.29 weight % solids, yielding 71 g suspension.

Example 18

A protected amino acrylamide monomer (N-fluorenylmethyloxycarbonyl-N'-acryloyl-piperazine) and is polymerized with tBDMS-HEAM monomer and tBDMS-EBHEAM crosslinker in a dispersed phase formed from polystyrene particles and is deprotected to form an amino hydrogel particle.

An emulsion is prepared by first dissolving 1.74 g SDS in 290.00 g water and then adding 14.50 g acetone and 29.00 g DOA. The emulsion is mixed by ultraturax for 2 minutes, and further homogenized for 5.6 minutes in a high pressure Gauline APV-100 homogenizer at 400 Bar.

41.33 g of this emulsion is added to 62.93 g of seed particles (seed diameter 0.126 μm, 4.59 weight % solids) in a flask. The mixture is shaken at 40° C. for 40 h in a shaking bath for activation.

An SDS borax solution is prepared by dissolving 4.54 g SDS and 9.69 g borax to 2369.8 g water.

A monomer emulsion is formed from 34.22 g 2-phenethyl acetate, 0.13 g AMBN, 4.98 g tBDMS HEAM, 1.61 g tBDMS-EBHEAM, 0.59 g N-fluorenylmethyloxycarbonyl-N'-acryloyl-piperazine and 221.71 g SDS borax solution mixed by ultraturax for 5 minutes, and further homogenized for 4 minutes.

In a 250 mL reactor, 17.09 g of a water dispersion of activated seed particles is mixed with 233.23 g of the monomer emulsion. The mixture is stirred and heated at 40° C. for 2 h. The mixture is further stirred and heated at 40° C. for another hour while argon gas (150-200 ml/min) is bubbled through the mixture. The amount of $O_2$ in the emulsion at this point is measure to be 62 ppb. The argon flow is stopped, and heating and stirring continued for 10 hours at 70° C.

The reaction mixture is transferred to a 250 mL centrifugation flask and centrifuged in a Beckman Coulter Avanti J-20 XP centrifuge for 60 minutes at 12000 RPM. The supernatant is discarded and the sediment is collected and transferred into a glass flask by adding water.

pH of the aqueous dispersion of gels is adjusted to 3.8 by adding 0.5 M acetic acid solution. The acidified gel dispersion is shaken at 60° C. in a shaking bath for 2.5 h and cooled.

The gel dispersion is transferred into a 1 L flask, 287.06 g THF is added, the flask is shaken at room temperature for 30 min on a shaking table and centrifuged in a Thermo Scientific Thermo Scientific Sorvall RC3CPlus centrifuge for 30 minutes at 4500 RPM. The upper phase of resulting biphasic mixture is discarded. 111.41 g THF is added, the flask is shaken at room temperature for 23 min on a shaking table and the flask is centrifuged for 30 minutes at 4500 RPM. Supernatant is discarded. DMF is added on the gel and the flask is shaken overnight at room temperature on a shaking table.

To the suspension of beads in DMF weighing 120 g, 10 mL piperidine is added and shaken at room temperature on a shaking table for 60 min. 45 g THF is added and the flask is centrifuged in a Beckman Coulter Avanti J-20 XP centrifuge for 90 minutes at 14000 RPM. Supernatant is discarded.

DMF is added till the suspension weighs 112 g and the gel is shaken on a shaking table for 4 h. 37 g THF is added and the flask is centrifuged in a Beckman Coulter Avanti J-20 XP centrifuge for 60 minutes at 14000 RPM. Supernatant is discarded.

DMF is added till the suspension weighs 130 g and the gel is shaken on a shaking table for 90 min. 40 g THF is added and the flask is centrifuged in a Beckman Coulter Avanti J-20 XP centrifuge for 60 minutes at 14000 RPM. Supernatant is discarded.

105 g dry 1-methyl-2-pyrrolidinone (NMP) is added on the batch and shaken for 3 days. The water swollen gel is analyzed in a disc centrifuge instrument (CPS Instruments, Inc, model DC20000) using a gradient of 3 and 7 w % sucrose solutions and a rotation speed of 15000 RPM. The diameter is measured as 0.3694 μm and CV (number) is measured as 4.8%.

Example 19

A protected amino acrylamide monomer ((9H-fluoren-9-yl)methyl(2-(2-(2-acrylamidoethoxy)ethoxy)ethyl)carbamate) and is polymerized with tBDMS-HEAM monomer and tBDMS-EBHEAM crosslinker in a dispersed phase formed from polystyrene particles and is deprotected to form an amino hydrogel particle.

An emulsion is prepared by first dissolving 1.68 g SDS in 280.00 g water and then adding 14.00 g acetone and 28.00 g DOA. The emulsion is mixed by ultraturax for 2 minutes, and further homogenized for 5.4 minutes in a high pressure Gauline APV-100 homogenizer at 400 Bar.

26.58 g of this emulsion is added to 52.61 g of seed particles (seed diameter 0.126 μm, 4.59 weight % solids) in a flask. The mixture is shaken at 40° C. for 16 h in a shaking bath for activation.

An SDS borax solution is prepared by dissolving 3.21 g SDS and 8.07 g borax to 1823.6 g water.

A monomer emulsion is formed from 33.68 g 2-phenethyl acetate, 0.13 g AMBN, 4.89 g tBDMS HEAM, 1.61 g tBDMS-EBHEAM, 0.64 g (9H-fluoren-9-yl)methyl(2-(2-(2-acrylamidoethoxy)ethoxy)ethyl)carbamate and 218.95 g SDS borax solution mixed by ultraturax for 5 minutes, and further homogenized for 2.6 minutes.

In a 250 mL reactor, 15.53 g of a water dispersion of activated seed particles is mixed with 234.9 g of the monomer emulsion. The mixture is stirred and heated at 40° C. for 2 h. The mixture is further stirred and heated at 40° C. for another hour while argon gas (150-200 ml/min) is bubbled through the mixture. The amount of $O_2$ in the emulsion at this point is measure to be 75 ppb. The argon flow is stopped, and heating and stirring continued for 10 hours at 70° C.

The reaction mixture is transferred to a 250 mL centrifugation flask and centrifuged in a Beckman Coulter Avanti J-20 XP centrifuge for 60 minutes at 13000 RPM. The supernatant is discarded and the sediment is collected and transferred into a glass flask by adding water.

pH of the aqueous dispersion of gels is adjusted to 3.7 by adding 0.5 M acetic acid solution. The acidified gel dispersion is shaken at 60° C. in a shaking bath for 2.5 h and cooled.

The gel dispersion is transferred into a 1 L flask, 180 g THF is added and centrifuged in a Thermo Scientific Thermo Scientific Sorvall RC3CPlus centrifuge for 30 minutes at 4500 RPM. The upper phase of resulting biphasic mixture is discarded and the mixture is shaken at room temperature for 15 min on a shaking table. 160 g THF is added and the flask is centrifuged for 30 minutes at 4500 RPM. Supernatant is discarded.

The gel is transferred into a glass flask with DMF. On 50 g of this DMF suspension of beads, 5 mL piperidine is added and the mixture is shaken at room temperature on a shaking table for 60 min.

50 g of this suspension is transferred to a 250 mL centrifuge flask and 23 g THF is added. The flask is centrifuged in a Beckman Coulter Avanti J-20 XP centrifuge for 10 minutes at 10000 RPM. Supernatant is discarded, DMF is added and the mixture is shaken on a shaking table for 16 h at room temperature.

Water swollen gel is analyzed in a disc centrifuge instrument (CPS Instruments, Inc, model DC20000) using a gradient of 3 and 7 w % sucrose solutions and a rotation speed of 15000 RPM. The diameter is measured as 0.4517 μm using a particle density of 1.032 g/ml. CV (number) is measured as 3.7%.

Example 20

A protected amino acrylamide monomer, N-Boc N-acryloyl-4,7,10-trioxatridecane-1,13-diamine, and is polymerized with tBDMS-HEAM monomer and tBDMS-EBHEAM crosslinker in a dispersed phase formed from polystyrene particles and is deprotected to form an amino hydrogel particle A PVA solution is prepared by slowly adding 80 g of 87-89% hydrolyzed polyvinylalcohol (PVA) to 2000 g water, stirring and heating to 80° C. for 1 hour and cooling. An amount of 67.66 g of the PVA solution is mixed with 582.70 g water, 0.62 g SDS and 2.74 g borax.

A monomer emulsion is formed from 26.39 g 2-phenethyl acetate, 0.098 g AMBN, 3.97 g tBDMS HEAM, 1.26 g tBDMS-EBHEAM, 0.21 g N-Boc N-acryloyl-4,7,10-trioxatridecane-1,13-diamine and 176.12 g PVA-borax solution mixed by ultraturax for few minutes, and further homogenized for 2 minutes.

In a 250 mL reactor, 7.15 g of a water dispersion of seed particles (seed diameter 0.319 μm, 8.07 weight % solids) is mixed with 193.02 g of the monomer emulsion. The mixture is stirred and heated at 40° C. for 2 h. The mixture is further stirred and heated at 40° C. for another hour while argon gas (150-200 ml/min) is bubbled through the mixture. The amount of $O_2$ in the emulsion at this point is measure to be 40 ppb. The argon flow is stopped, and heating and stirring continued for 10 hours at 70° C.

The reaction mixture is transferred to a 250 mL centrifugation flask and centrifuged in a Beckman Coulter Avanti J-20 XP centrifuge for 40 minutes at 12500 RPM. The supernatant is discarded and the sediment is collected and transferred into a glass flask by adding water.

1 M $H_2SO_4$ solution is added on the gel suspension in a 9:1 vol ratio to end up in 0.1 M $H_2SO_4$ concentration. The suspension is shaken at 60° C. for 3 h and cooled down to room temperature.

Concentrated NaOH solution is added dropwise till the pH reaches 12. 500 g THF is added to the suspension, divided into two 250 mL bottles and the mixtures are shaken at room temperature for 60 min on a shaking table. The flasks are centrifuged in a Thermo Scientific Sorvall RC3CPlus centrifuge for 30 minutes at 4500 RPM. The upper phases of resulting biphasic mixtures are discarded, water is added to each flask and the flasks are shaken at room temperature overnight on a shaking table. pH of the mixtures are adjusted to 12.3 by adding concentrated NaOH solution, the flasks are shaken at room temperature for 25 min on a shaking table and the flasks are centrifuged for 30 minutes at 4500 RPM in a Beckman Coulter Avanti J-20 XP centrifuge. Supernatants are discarded.

Water is added to each flask and pH of the mixtures are adjusted to 12.2 by adding concentrated NaOH solution. The flasks are shaken at room temperature overnight on a shaking table and the flasks are centrifuged for 30 minutes at 4000 RPM in a Thermo Scientific Sorvall RC3CPlus centrifuge. Supernatants are discarded.

Water is added to each flask, the flasks are shaken at room temperature for 4 h on a shaking table and the flasks are centrifuged for 30 minutes at 6500 RPM in a Beckman Coulter Avanti J-20 XP centrifuge. Supernatants are discarded NMP is added to each flask, the flasks are shaken at room temperature overnight on a shaking table and the flasks are centrifuged for 30 minutes at 4500 RPM in a Thermo Scientific Sorvall RC3CPlus centrifuge. Approximately half of supernatants are discarded.

The gel sediments are combined into one bottle, NMP added and the flasks are centrifuged for 60 minutes at 4500 RPM in a Thermo Scientific Sorvall RC3CPlus centrifuge. Supernatants are discarded NMP is added to the flask, the flask is shaken at room temperature for 3 h on a shaking table and the flasks are centrifuged for 50 minutes at 6500 RPM in a Beckman Coulter Avanti J-20 XP centrifuge. Supernatants are discarded.

Some more NMP is added and the solids content of the dispersion is determined to be 0.108%. The diameter of a water swollen gel is measured in a microscope with phase contrast equipment and is on average 1.79 μm Water swollen gel is further analyzed in a disc centrifuge instrument (CPS Instruments, Inc, model DC20000) using a gradient of 3 and 7 w % sucrose solutions and a rotation speed of 10050 RPM. The diameter is measured as 0.934 μm using a particle density of 1.032 g/ml.

Example 21

A protected amino acrylamide monomer, N-Boc N-acryloyl-4,7,10-trioxatridecane-1,13-diamine, and is polymerized with tBDMS-HEAM monomer and tBDMS-EBHEAM crosslinker in a dispersed phase formed from polystyrene particles and is deprotected to form an amino hydrogel particle An emulsion is prepared by first dissolving 1.74 g SDS in 290.00 g water and then adding 14.50 g acetone and 29.00 g bis(2-ethylhexyl) adipate (DOA). The emulsion is mixed by ultraturax for 2 minutes, and further homogenized for 5.6 minutes in a high pressure Gauline APV-100 homogenizer at 400 Bar.

26.58 g of this emulsion is added to 52.27 g of seed particles (seed diameter 0.126 μm, 4.59 weight % solids) in a flask. The mixture is shaken at 40° C. for 40 h in a shaking bath for activation.

An SDS borax solution is prepared by dissolving 1.87 g SDS and 4.04 g borax to 987.5 g water.

A monomer emulsion is formed from 62.81 g 2-phenethyl acetate, 0.238 g AMBN, 9.13 g tBDMS HEAM, 3.00 g tBDMS-EBHEAM, 1.05 g N-Boc N-acryloyl-4,7,10-trioxatridecane-1,13-diamine and 408.39 g SDS-borax solution mixed by ultraturax for few minutes, and further homogenized for 4.8 minutes.

In a 500 mL reactor, 31.06 g of a water dispersion of activated seed particles is mixed with 469.6 g of the monomer emulsion. The mixture is stirred and heated at 40° C. for 2 h. The mixture is further stirred and heated at 40° C. for another hour while argon gas (200 ml/min) is bubbled through the mixture. The argon flow is stopped, and heating and stirring continued for 10 hours at 70° C.

The reaction mixture is transferred to four 250 mL centrifugation flasks and centrifuged in a Beckman Coulter Avanti J-20 XP centrifuge for 60 minutes at 13000 RPM. The supernatants are discarded and the sediments are collected and transferred into a glass flask by adding water.

pH of the aqueous dispersion of gels is adjusted to 3.8 by adding 0.5 M acetic acid solution. The acidified gel dispersion is shaken at 60° C. in a shaking bath for 2 h and cooled.

1 M $H_2SO_4$ solution is added on the gel suspension in a 9:1 vol ratio to end up in 0.1 M $H_2SO_4$ concentration. The suspension is shaken at 60° C. for 3 h and cooled down to room temperature.

Concentrated NaOH solution is added dropwise till the pH reaches 12. The suspension is divided into two 1 L centrifuge flasks. 380 g THF is added to each flask, and the mixtures are shaken at room temperature for 145 min on a shaking table. The flasks are centrifuged in a Thermo Scientific Sorvall RC3CPlus centrifuge for 30 minutes at 4500 RPM. Supernatants are discarded, water is added to each flask and the flasks are shaken at room temperature for 2 h on a shaking table. More water is added and the flasks are centrifuged in a Thermo Scientific Sorvall RC3CPlus centrifuge for 60 minutes at 4500 RPM. Supernatants are discarded.

The gel is transferred into four 250 mL centrifuge flasks and the flasks are centrifuged for 45 minutes at 14500 RPM in a Beckman Coulter Avanti J-20 XP centrifuge. Supernatants are discarded.

Water is added to each flask, the flasks are shaken at room temperature for 60 min on a shaking table and the flasks are centrifuged for 45 minutes at 14500 RPM in a Beckman Coulter Avanti J-20 XP centrifuge. Supernatants are discarded.

Water is added to each flask and pH of the mixtures are adjusted to 12 by adding concentrated NaOH solution. The flasks are shaken at room temperature for 25 min on a shaking table and the flasks are centrifuged for 30 minutes at 6500 RPM in a Beckman Coulter Avanti J-20 XP centrifuge. Supernatants are discarded.

Water is added to each flask and pH of the mixtures are adjusted to 12.3 by adding concentrated NaOH solution. The flasks are shaken at room temperature overnight on a shaking table and the flasks are centrifuged for 30 minutes at 4000 RPM in a Thermo Scientific Sorvall RC3CPlus centrifuge. Supernatants are discarded.

Water is added to each flask, the flasks are shaken at room temperature for 4 h on a shaking table and the flasks are centrifuged for 30 minutes at 6500 RPM in a Beckman Coulter Avanti J-20 XP centrifuge. Supernatants are discarded.

NMP is added to each flask, the flasks are shaken at room temperature overnight on a shaking table and the flasks are centrifuged for 30 minutes at 4500 RPM in a Thermo Scientific Sorvall RC3CPlus centrifuge. Supernatants are discarded.

NMP is added to the flasks, the flasks are shaken at room temperature for 5 h on a shaking table and the flasks are centrifuged for 50 minutes at 6500 RPM in a Beckman Coulter Avanti J-20 XP centrifuge. Supernatants are discarded.

Some more NMP is added and the solids content of the dispersion is determined to be 0.408%. The diameter of a water swollen gel is measured in a microscope with phase contrast equipment and is on average 0.86 µm. The diameter of a water swollen gel is also measured in disc centrifuge instrument (CPS Instruments, Inc, model DC20000) using a gradient of 3 and 7 w % sucrose solutions and a rotation speed of 15000 RPM. The diameter is measured as 0.511 µm using a particle density of 1.032 g/ml. CV (number) is measured as 4.82%.

Example 22 tBDMS-HEAM is polymerized with tBDMS-EBHEAM crosslinker in a dispersed phase formed from polystyrene particles and is deprotected to form a hydrogel particle.

An emulsion is prepared by first dissolving 1.14 g SDS in 190.00 g water and then adding 28.50 g acetone and 19.00 g DOA. The emulsion is mixed by ultraturax for 5 minutes, and further homogenized for 4 minutes in a high pressure Gauline APV-100 homogenizer at 400 Bar.

30.55 g of this emulsion is added to 7.39 g of seed particles (seed diameter 4.96 µm, 9.54 weight % solids) in a flask. The mixture is shaken at 40° C. for 22 h in a shaking bath for activation.

300 g $H_2O$ is heated up to 80° C. and 4.2 g Methocel K-100 is dissolved in. 332 g $H_2O$ is added to obtain the Methocel K-100 solution.

2.41 g borax is added onto 94.8 g Methocel solution. The weight of this solution is totaled up to 420.2 g by adding water to obtain the borax solution is prepared by mixing A monomer emulsion is formed from 35.72 g 2-phenethyl acetate, 0.138 g AMBN, 5.56 g tBDMS HEAM, 1.71 g tBDMS-EBHEAM and 165.89 g borax solution mixed by ultraturax for few minutes, and further homogenized for 2.1 minutes.

In a 250 mL reactor, 9.25 g of a water dispersion of activated seed particles is mixed with 177.0 g of the monomer emulsion and 63.26 g Methocel K-100 solution. The mixture is stirred and heated at 40° C. for 2.5 h. The mixture is further stirred and heated at 40° C. for another 30 min while argon gas (200 ml/min) is bubbled through the mixture. The argon flow is stopped, and heating and stirring continued for 10 hours at 70° C.

Part of the reaction mixture is transferred to a 250 mL centrifugation flask and centrifuged in a Beckman Coulter Avanti J-20 XP centrifuge for 60 minutes at 13000 RPM. The supernatant is discarded and the sediment is collected and transferred into a glass flask by adding water.

pH of the aqueous dispersion of gels is adjusted to 3.8 by adding 0.5 M acetic acid solution. The acidified gel dispersion is shaken at 60° C. in a shaking bath for 150 min and cooled.

The gel dispersion is transferred into a 1 L flask, 300 g THF is added, and the flask is shaken at room temperature for 30 min on a shaking table and centrifuged in a Thermo Scientific Sorvall RC3CPlus centrifuge for 25 minutes at 4500 RPM. The upper phase of resulting biphasic mixture is discarded, 50 g THF is added to the flask. The flask is shaken at room temperature for 30 min on a shaking table and centrifuged for 25 minutes at 4500 RPM. Supernatant is discarded.

Contents of the flask are divided into two 250 mL centrifuge flasks. Approximately 100 g DMF is added on each flask and the flasks are shaken overnight at room temperature on a shaking table. Contents of each flask are totaled to 200 g by adding 20 g THF and an amount of DMF. The flasks are centrifuged in a Beckman Coulter Avanti J-20 XP centrifuge for 70 minutes at 13000 RPM. Supernatants are discarded.

Approximately 100 g DMF is added on each flask and the flasks are shaken for 40 min at room temperature on a shaking table. Contents of each flask are totaled to 200 g by adding 20 g THF and an amount of DMF. The flasks are centrifuged in a Beckman Coulter Avanti J-20 XP centrifuge for 70 minutes at 13000 RPM. Supernatants are discarded and all the sediments are combined into a new flask by using minimal amounts of DMF.

The solids content of the dispersion is determined to be 2.34 g. The diameter of water swollen gels is measured in a microscope with phase contrast equipment and is on average 47.5 µm.

Example 23 tBDMS-HEAM monomer is polymerized in an aqueous emulsion to form monosized seed particles.

250 mL of water is boiled in a 250 mL conical flask for 10 minutes and cooled down with ice-water bath while purging Ar gas into.

In a 50 mL conical flask, 0.04 g SDS is dissolved in 10.1 g of this boiled water by using a magnetic stirbar.

In another 50 mL conical flask, 0.059 g potassium persulfate is dissolved in 10 g of the boiled water by using a magnetic stirbar.

Into a 100 mL jacketed two-piece reactor equipped with a mechanical stirrer, a temperature probe, a water running condenser and an Ar source, 0.20 g borax and 80 g of boiling water, boiled previously for at least 30 min, are added and the reactor is heated to 80° C. by using a heating bath while the overhead stirrer equipped with a poly(tetrafluoroethylene) blade is set to stir at 150±5 RPM. The solution is purged with Ar for 20 min.

When the temperature of the solution reaches 80° C., the Ar tubing is lifted out of the solution with Ar pressure is still on and the SDS solution, ultrasonicated for 5 min right before, is added into the reactor.

8 min after the addition of SDS solution, the mechanical stirrer is set to stir at 250±5 RPM.

9.22 g tBDMS-HEAM is purged with Ar for 5 min and then added into the reactor. 1 min after the addition of tBDMS-HEAM, the mechanical stirrer is set to stir at 350±5 RPM.

5 min after the addition of tBDMS-HEAM, potassium persulfate solution, purged with Ar for 5 min right before, is added quickly into the reactor and the reactor is sealed while Ar flow is still running above the emulsion.

270 min after the addition of potassium persulfate, mechanical stirrer is set to stir at 250±5 RPM and the Ar flow is stopped. The emulsion is further polymerized for 18 h.

The batch is cooled down to room temperature and the whole batch is transferred into a plastic bottle. The diameter is measured by dynamic light scattering (Malvern, Nano ZS) and found to be 0.398 μm. PDI is measured to be 0.015. Weight average molecular weight and number average molecular weights are measured to be 707 kDa and 102 kDa, respectively, by using a gel permeation chromatography instrument (Waters 717plus equipped with a Waters 2414 refractive index detector and Polymer Laboratories 5 μm Mixed-C 300 mm×7.5 mm columns).

The CV of the particle is measured in disc centrifuge instrument (CPS Instruments, Inc, model DC20000) using a gradient of 3 and 7 w % sucrose solutions and a rotation speed of 20 000 RPM and found to be 2.0%.

Example 24

Activation of an amino-hydrogel and conjugation of the hydrogel with amine terminal DNA probe.

To a solution of 100 billion of amino-hydrogel (diameter=0.55 microns, 23 million amines/micron3) in anhydrous, amine-free N-methylpyrrolidone (NMP) (6004), solid bis-succinimidyl suberate (22.1 mg, 60 μmole) is added followed by tributylamine (14 μL, 60 μmole). After stirring at 60° C. for 1 h, the hydrogels are isolated by centrifugation (30 min at 21300 rcf). The hydrogel pellet is diluted with amine-free anhydrous NMP (1 ml) and is isolated by centrifugation; this washing process is repeated 2 times, and the final pellet is re-suspended in NMP (600 μL). This hydrogel suspension is treated with acetic anhydride (304, 317 μmole) and tributylamine (30 μL, 126 μmole), and stirred at room temperature for 2 h. The resulting hydrogel is isolated by centrifugation (30 min at 21300 rcf) and the pellet is diluted with amine-free anhydrous NMP (1 ml) and is isolated by centrifugation; this washing process is repeated 2 times, and the final activated, capped pellet is diluted with 1 μmole of a 3 μmolar NMP solution of tetrabutylammonium 5'-amino-oligonucleotide, tributylamine (1 μmole), and amine-free NMP to a final volume of 600 μL. After stirring at 70° C. for 16 h, the DNA conjugated hydrogel is isolated by centrifugation (30 min at 21300 rcf). The pellet is washed with NMP (1 ml), followed by Deionized water wash (1 ml) using centrifugation to isolate the pellets. The final hydrogel pellet is diluted with 1×TE buffer (1.6 ml) and stirred at 80° C. for 1 h. The hydrogels are isolated by centrifugation (30 min at 21300 rcf) and washed twice with DI water (1 ml) (using centrifugation for pellet isolation). To the final pellet is added 30% aqueous ammonia; after 15 minutes at room temperature, the hydrogel is isolated centrifugation (20 min at 21300 rcf) and is washed 3× with DI water (1 mL) using centrifugation for isolation. The final pellet is re-dispersed in the buffer desired for performing target amplification.

Example 25

An oligonucleotide is directly conjugated to a mesyl activated particle. Mesyl chloride activated microgels are prepared via seeded emulsion polymerization. Thus formed particles are washed in N-methyl-2-pyrrolidone (NMP) in preparation for conjugation with ion exchanged single stranded DNA.

The sodium salt of 5'-NH2-C6-30-mer oligonucleotide was dissolved in 0.1 M tetrabutylammonium acetate, and injected onto a reverse phase HPLC column. Elution was performed with 0.1 M tetrabutylammonium acetate mobile phase. The fraction containing nucleic acid was collected, lyophilized to a dry powder, and re-suspended in dry N-methyl-2-pyrrolidone (NMP).

Five million particles ($5.0 \times 10^9$) are dispersed in 350 uL of anhydrous NMP and vortex mixed to disperse. 124 uL of Bu4NAc-DNA (5'-NH2-C6-30-mer oligonucleotide) in NMP (4.10 mM) is directly added to the particle mixture. 19.5 uL of tetraethylammonium borate (26.14 mM) is then added to the reaction mixture for a final volume of ~500 uL.

The reaction mixture is quickly vortex mixed and is gently mixed at 70° C. for 16 hours. The mixture is centrifuged, the supernatant is decanted, and the particles are re-suspended in 1 mL of NMP. After vortex mixing, the re-suspended microgel particles are pelleted with two cycles of precipitation/dispersion in NMP. After the second NMP wash, the pellets are brought up in 1 mL of 2×SSPE/0.1% sodium dodecyl sulfate (SDS), mixed and centrifuged to pellets. Finally, the particles are brought up in 1 mL of 1×PBS/0.1% Triton X-100, mixed and centrifuged to a firm pellet, repeating this process three times. After the final cycle, the conjugated microgels are re-suspended in 500 uL 1×PBS/0.1% Triton X-100.

In a first aspect, a method of forming a particle includes, in a disperse phase within an aqueous suspension, polymerizing a plurality of mer units of a hydrophilic monomer having a hydrophobic protection group, thereby forming a polymeric particle including a plurality of the hydrophobic protection groups, and converting the polymeric particle to a hydrogel particle.

In an example of the first aspect, converting the polymeric particle includes removing at least a portion of the plurality of the hydrophobic protection groups from the polymeric particle. For example, removing at least a portion of the plurality of the hydrophobic protection groups includes acid cleaving at least a portion of the plurality of the hydrophobic protection groups from the polymeric particle.

In another example of the first aspect and the above examples, converting the polymeric particle includes removing substantially all of the plurality of hydrophobic protection groups from the polymeric particle.

In a further example of the first aspect and the above examples, the method further includes promoting a seed particle in the aqueous suspension to form the dispersed phase. In an example, the mass ratio of protected monomer:seed particles is in a range of 150:1 to 1:1, such as a range of 50:1 to 1:1. In another example, the seed particle includes a seed polymer. The method can further include extracting the seed polymer after converting the polymeric particle. In an example, the seed polymer can be hydrophobic. In another example, the seed polymer includes a styrenic polymer, an acrylic polymer, another vinyl polymer, or a combination thereof. In a particular example of the above examples, the seed particle has an initial particle size of not greater than 0.6 micrometers, such as not greater than 0.45 micrometers, not greater than 0.35 micrometers, or not greater than 0.15 micrometers. In another example of the above examples, promoting the seed particle includes mixing a solvent and a promoting agent with the seed particle. For example, the promoting agent is hydrophobic. In another example, the promoting agent includes dioctanoyl peroxide.

In an additional example of the first aspect and the above examples, the hydrophilic monomer includes an acrylamide.

In another example of the first aspect and the above examples, the hydrophobic protection group includes a hydroxyl protection group.

In a further example of the first aspect or the above examples, the hydrophobic protection group includes an organometallic moiety. For example, the organometallic moiety forms a silyl ether functional group. In an example, the silyl ether function group is derived from tert-butyldimethylsilane ether, trimethylsilyl ether, triethylsilyl ether, diphenyl methyl silyl ether, or a combination thereof.

In an example of the first aspect and the above examples, polymerizing the plurality of mer units further includes mixing a crosslinker with the hydrophilic monomer having a hydrophobic protection group. For example, mixing the crosslinker can include mixing the crosslinker at a mass ratio of hydrophilic monomer:crosslinker in a range of 15:1 to 1:2. The range can be 10:1 to 1:1. In another example, the crosslinker is a low water solubility crosslinker. In an example of the above examples, the crosslinker is a divinyl crosslinker. For example, the divinyl crosslinker includes a diacrylamide. In a particular example of the above examples, the diacrylamide includes N,N'-(ethane-1,2-diyl)bis(N-(2-((tert-butyldimethylsilyl)oxy)ethyl)acrylamide, N,N'-(2-hydroxypropane-1,3-diyl)diacrylamide, a protected derivative thereof, or a combination thereof. The diacrylamide can, for example, include N,N'-(ethane-1,2-diyl)bis(N-(2-((tert-butyldimethylsilyl)oxy)ethyl)acrylamide, N,N'-(N-(2-((tert-butyldimethylsilyl)oxy)propane-1,3-diyl)diacrylamide, N,N'-(ethane-1,2-diyl)bis(N-(2-((triethylsilyl)oxy)ethyl)acrylamide, N,N'-(N-(2-((triethylsilyl)oxy)propane-1,3-diyl)diacrylamide, silyl-protected N-[2-(acryloylamino)-1,2-dihydroxyethyl]acrylamide such as N,N'(2,3-bis((triethylsilyl)oxy)butane-1,4-diyl)diacrylamide, or a combination thereof. In another example of the above examples, the divinyl crosslinker includes ethyleneglycoldimethacrylate, divinylbenzene, hexamethylene bisacrylamide, trimethylolpropane trimethacrylate, or a combination thereof.

In another example of the first aspect and the above examples, polymerizing the plurality of mer units includes mixing a porogen with the hydrophilic monomer having a hydrophobic protection group. For example, the porogen can be an aromatic porogen. In an example, the aromatic porogen includes toluene.

In an additional example of the first aspect and the above examples, the method further includes activating the hydrogel particle. In an example, converting includes providing one or more hydroxyl groups on the hydrogel particle and wherein activating includes converting at least one of the one or more hydroxyl groups to a sulfonate ester group. For example, converting can include providing one or more hydroxyl groups on the hydrogel particle and wherein activating includes replacing at least one of the one or more hydroxyl groups with an azide functional moiety. In another example, the method further includes binding an oligonucleotide to the activated hydrogel polymer. For example, binding includes nucleophilic substitution and the oligonucleotide is a nucleophile-terminated oligonucleotide. A nucleophile of the nucleophile-terminated oligonucleotide can be an amine group. A nucleophile of the nucleophile-terminated oligonucleotide can be a thiol group. In an example of the above example, the method further includes hybridizing a polynucleotide to the oligonucleotide. For example, the method can further include amplifying the polynucleotide into a plurality of polynucleotides and attaching at least a portion of the plurality of polynucleotides to the hydrogel particle, thereby generating a hydrogel particle including a plurality of attached polynucleotides. Alternatively, the method can further include amplifying the polynucleotide into a plurality of complementary polynucleotides by extending the oligonucleotide, thereby generating a hydrogel particle including a plurality of attached polynucleotides.

In another example of the first aspect and the above examples, the hydrogel particle is one of a plurality of similarly formed hydrogel particles having an average particle size of not greater than 2 micrometer. For example, the average particle size can be not greater than 1 micrometer, such as not greater than 0.8 micrometers, or not greater than 0.5 micrometers.

In a further example of the first aspect and the above examples, the hydrogel particle is one of a plurality of similarly formed hydrogel particles that are substantially uniform in size.

In an additional example of the first aspect or the above examples, the hydrogel particle is one of a plurality of similarly formed hydrogel particles having a coefficient of variance of not greater than 5.0%. For example, the coefficient of variance of not greater than 3.5%.

In a second aspect, a method of forming a particle includes, in a disperse phase within an aqueous suspension, polymerizing a plurality of mer units of an acrylamide monomer having a hydrophobic protection group, thereby forming a polymeric particle including a plurality of the hydrophobic protection groups, and converting the polymeric particle to a hydrophilic particle.

In an example of the second aspect, converting the polymeric particle includes removing at least a portion of the plurality of the hydrophobic protection groups from the polymeric particle. For example, removing at least a portion of the plurality of the hydrophobic protection groups includes acid cleaving at least a portion of the plurality of the hydrophobic protection groups from the polymeric particle.

In another example of the second aspect or the above examples, converting the polymeric particle includes removing substantially all of the plurality of hydrophobic protection groups from the polymeric particle.

In an additional example of the second aspect or the above examples, the method further includes promoting a seed particle in the aqueous suspension to form the dispersed phase. For example, the mass ratio of protected monomer:seed particles is in a range of 50:1 to 1:1. In another example, the seed particle includes a seed polymer. In an example of the above examples, the method further includes extracting the seed polymer after converting the polymeric particle. The seed polymer can be hydrophobic. In another example, the seed polymer includes a styrenic polymer, an acrylic polymer, another vinyl polymer, or a combination thereof. In an example of the above examples, the seed particle has an initial particle size of not greater than 0.6 micrometers. In an additional example of the above examples, promoting the seed particle includes mixing a solvent and a promoting agent with the seed particle. For example, the promoting agent can be hydrophobic.

In another example of the second aspect or the above examples, the hydrophobic protection group includes a hydroxyl protection group. In an additional example of the second aspect and the above examples, the hydrophobic protection group includes an organometallic moiety. For example, the organometallic moiety can form a silyl ether functional group. In an example, the silyl ether function group can be derived from tert-butyldimethylsilane ether, trimethylsilyl ether, triethylsilyl ether, diphenyl methyl silyl ether, or a combination thereof.

In a further example of the second aspect and the above examples, polymerizing the plurality of mer units further includes mixing a crosslinker with the acrylamide monomer having a hydrophobic protection group. Mixing the crosslinker can include mixing the crosslinker at a mass ratio of hydrophilic monomer:crosslinker in a range of 15:1 to 1:2. In an example, the crosslinker is a low water solubility crosslinker. In another example, the crosslinker is a divinyl crosslinker.

In an additional example of the second aspect and the above examples, polymerizing the plurality of mer units includes mixing a porogen with the acrylamide monomer having a hydrophobic protection group. For example, the porogen can include an aromatic porogen.

In another example of the second aspect and the above examples, the method further includes activating the hydrophilic particle. In an example, converting includes providing one or more hydroxyl groups on the hydrogel particle and wherein activating includes converting at least one of the one or more hydroxyl groups to a sulfonate ester group. In another example, converting includes providing one or more hydroxyl groups on the hydrogel particle and wherein activating includes replacing at least one of the one or more hydroxyl groups with an azide functional moiety. In an additional example, the method further includes binding an oligonucleotide to the activated hydrogel polymer. Binding can include nucleophilic substitution and the oligonucleotide is a nucleophile-terminated oligonucleotide. A nucleophile of the nucleophile-terminated oligonucleotide can be an amine group. In another example, a nucleophile of the nucleophile-terminated oligonucleotide can include a thiol group. In an additional example, the method further includes hybridizing a polynucleotide to the oligonucleotide. In another example, the method further includes amplifying the polynucleotide into a plurality of polynucleotides and attaching at least a portion of the plurality of polynucleotides to the hydrophilic particle, thereby generating a hydrophilic particle including a plurality of attached polynucleotides. Alternatively, the method can further include amplifying the polynucleotide into a plurality of complementary polynucleotides by extending the oligonucleotide, thereby generating a hydrogel particle including a plurality of attached polynucleotides.

In a further example of the second aspect and the above examples, the hydrophilic particle is one of a plurality of similarly formed hydrophilic particles having an average particle size of not greater than 2 micrometer.

In an additional example of the second aspect and the above examples, the hydrophilic particle is one of a plurality of similarly formed hydrophilic particles that are substantially uniform in size.

In another example of the second aspect and the above examples, the hydrophilic particle is one of a plurality of similarly formed hydrophilic particles having a coefficient of variance of not greater than 5.0%.

In a third aspect, a method of forming a particle includes, in a disperse phase within an aqueous suspension, polymerizing a plurality of mer units of an radically polymerizable monomer with a diacrylamide crosslinker having a hydrophobic protection group, thereby forming a polymeric particle including a plurality of the hydrophobic protection groups. The method further includes removing at least a portion of plurality of the hydrophobic protection groups.

In an example of the third aspect, the diacrylamide includes N,N'-(ethane-1,2-diyl)bis(N-(2-((tert-butyldimethylsilyl)oxy)ethyl)acrylamide, N,N'-(2-hydroxypropane-1,3-diyl) diacrylamide, a protected derivative thereof, or a combination thereof. The diacrylamide can, for example, include N,N'-(ethane-1,2-diyl)bis(N-(2-((tert-butyldimethylsilyl)oxy) ethyl)acrylamide, N,N'-(N-(2-((tert-butyldimethylsilyl)oxy) propane-1,3-diyl)diacrylamide, N,N'-(ethane-1,2-diyl)bis (N-(2-((triethylsilyl)oxy)ethyl)acrylamide, N,N'-(N-(2-((triethylsilyl)oxy)propane-1,3-diyl)diacrylamide, silyl-protected N-[2-(acryloylamino)-1,2-dihydroxyethyl] acrylamide such as N,N'(2,3-bis((triethylsilyl)oxy)butane-1, 4-diyl)diacrylamide, or a combination thereof.

In another example of the third aspect or the above examples, polymerizing includes mixing the diacrylamide crosslinker at a mass ratio of radically polymerizable: crosslinker in a range of 15:1 to 1:2.

In an additional example of the third aspect or the above examples, removing at least a portion of the plurality of the hydrophobic protection groups includes acid cleaving at least a portion of the plurality of the hydrophobic protection groups from the polymeric particle.

In a further example of the third aspect or the above examples, the radically polymerizable monomer is a vinyl-based monomer. In an example, the vinyl-based monomer includes an acrylate, an acrylamide, a vinyl alcohol, a vinyl acetate, acrylamido-methyl-propanesulfonic acid, or a combination thereof. For example, the vinyl-based monomer is an acrylamide.

In another example of the third aspect or the above examples, the method further includes promoting a seed particle in the aqueous suspension to form the dispersed phase. For example, the mass ratio of protected monomer:seed particles is in a range of 50:1 to 1:1. In another example, the seed particle includes a seed polymer. In a further example, the method further includes extracting the seed polymer after converting the polymeric particle. In an example, the seed polymer is hydrophobic. In another example, the seed polymer includes a styrenic polymer, an acrylic polymer, another vinyl polymer, or a combination thereof. In an additional example, the seed particle has an initial particle size of not greater than 0.6 micrometers. In another example, promoting the seed particle includes mixing a solvent and a promoting agent with the seed particle.

In a further example of the third aspect or the above examples, the hydrophobic protection group includes a hydroxyl protection group.

In an additional example of the third aspect or the above examples, the hydrophobic protection group includes an organometallic moiety. In an example, the organometallic moiety forms a silyl ether functional group. In another example, the silyl ether function group is derived from tert-butyldimethylsilane ether, trimethylsilyl ether, triethylsilyl ether, diphenyl methyl silyl ether, or a combination thereof.

In another example of the third aspect or the above examples, polymerizing the plurality of mer units includes mixing a porogen with the radically polymerizable monomer and the diacrylamide crosslinker. For example, the porogen can be an aromatic porogen.

In a further example of the third aspect or the above examples, the method further includes activating the hydrophilic particle. For example, the method further includes binding an oligonucleotide to the activated hydrogel polymer. In another example, binding includes nucleophilic substitution and the oligonucleotide is a nucleophile-terminated oligonucleotide. For example, a nucleophile of the nucleophile-terminated oligonucleotide is an amine group. In a further example, a nucleophile of the nucleophile-terminated oligonucleotide is a thiol group. In another example, the method further includes hybridizing a polynucleotide to the oligonucleotide. In an additional example, the method further includes amplifying the polynucleotide into a plurality of polynucleotides and attaching at least a portion of the plurality of polynucleotides to the hydrophilic particle, thereby generating a hydrophilic particle including a plurality of attached polynucleotides. Alternatively, the method can further include amplifying the polynucleotide into a plurality of complementary polynucleotides by extending the oligonucleotide, thereby generating a hydrogel particle including a plurality of attached polynucleotides.

In an additional example of the third aspect or the above examples, the hydrophilic particle is one of a plurality of similarly formed hydrophilic particles having an average particle size of not greater than 2 micrometer.

In another example of the third aspect or the above examples, the hydrophilic particle is one of a plurality of similarly formed hydrophilic particles having a coefficient of variance of not greater than 5.0%.

In a fourth aspect, a method of forming a particle includes polymerizing a plurality of mer units of a hydrophilic monomer having a hydrophobic protection group, thereby forming a polymeric particle including a plurality of the hydrophobic protection groups; removing at least a portion of plurality of the hydrophobic protection groups from the polymeric particle to form a hydrophilic particle; and binding an oligonucleotide to the hydrophilic particle.

In an example of the fourth aspect or the above examples, removing at least a portion of the plurality of the hydrophobic protection groups includes acid cleaving at least a portion of the plurality of the hydrophobic protection groups from the polymeric particle.

In another example of the fourth aspect or the above examples, the hydrophilic monomer includes an acrylamide.

In an additional example of the fourth aspect or the above examples, the hydrophobic protection group includes a hydroxyl protection group.

In a further example of the fourth aspect or the above examples, the hydrophobic protection group includes an organometallic moiety. For example, the organometallic moiety can form a silyl ether functional group.

In an example of the fourth aspect or the above examples, polymerizing the plurality of mer units further includes mixing a crosslinker with the hydrophilic monomer having a hydrophobic protection group. For example, the crosslinker can be a divinyl crosslinker. In another example, the divinyl crosslinker includes a diacrylamide.

In another example of the fourth aspect or the above examples, the method further includes activating the hydrogel particle prior to binding the oligonucleotide. For example, removing can includes providing one or more hydroxyl groups on the hydrophilic particle and wherein activating includes converting at least one of the one or more hydroxyl groups to a sulfonate ester group. In another example, removing includes providing one or more hydroxyl groups on the hydrophilic particle and wherein activating includes replacing at least one of the one or more hydroxyl groups with an azide functional moiety. In an additional example, binding includes binding the oligonucleotide to the activated hydrogel polymer. In an additional example, binding includes nucleophilic substitution and the oligonucleotide is a nucleophile-terminated oligonucleotide. For example, a nucleophile of the nucleophile-terminated oligonucleotide can be an amine group. In another example, a nucleophile of the nucleophile-terminated oligonucleotide can include a thiol group.

In a further example of the fourth aspect or the above examples, the method further includes hybridizing a polynucleotide to the oligonucleotide. For example, the method further includes amplifying the polynucleotide into a plurality of polynucleotides and attaching at least a portion of the plurality of polynucleotides to the hydrogel particle, thereby generating a hydrogel particle including a plurality of attached polynucleotides. Alternatively, the method can further include amplifying the polynucleotide into a plurality of complementary polynucleotides by extending the oligonucleotide, thereby generating a hydrogel particle including a plurality of attached polynucleotides.

In a fifth aspect, a plurality of particles includes at least 100,000 particles. At least one particle of the plurality of particles includes a hydrogel. The plurality of particles have an average particle size of not greater than 100 micrometers and a coefficient of variance of not greater than 5%. For example, the coefficient of variance is not greater than 4.5%, such as not greater than 4.0%, not greater than 3.5%, or not greater than 3.0%.

In an example of the fifth aspect or the above examples, the average size is not greater than 30 micrometers, such as not greater than 1.5 micrometers, not greater than 1.1 micrometers, not greater than 0.6 micrometers, or not greater than 0.5 micrometers.

In another example of the fifth aspect or the above examples, the hydrogel includes an acrylamide polymer.

In a further example of the fifth aspect or the above examples, the particles of the plurality of particles have an average porosity of at least 60%.

In a sixth aspect, a system includes an array of wells. At least one well of the array of wells is operatively connected with an ISFET sensor. The system further includes a plurality of hydrogel particles having a coefficient of variance of not greater than 5%. At least one of the hydrogel particles of the plurality of hydrogel particles is disposed in a well of the array of wells.

In a seventh aspect, a plurality of particles is formed by the method including, in a disperse phase within an aqueous suspension, polymerizing a plurality of mer units of a hydrophilic monomer having a hydrophobic protection group, thereby forming a polymeric particle including a plurality of the hydrophobic protection groups, and including converting the polymeric particle to a hydrogel particle.

In an example of the seventh aspect, the plurality of particles have a coefficient of variance of not greater than 5.0%, such as not greater than 4.0%, not greater than 3.5%, or not greater than 3.0%.

In another example of the seventh aspect or the above examples, the plurality of particles having an average size of not greater than 100 micrometers. For example, the average size can be not greater than 30 micrometers, such as not greater than 1.5 micrometers, or not greater than 0.8 micrometers.

In an additional example of the seventh aspect or the above examples, the hydrophilic monomer includes an acrylamide monomer.

In a further example of the seventh aspect or the above examples, the particles of the plurality of particles have an average porosity of at least 60%.

In an eighth aspect, a composition includes an aqueous mixture of an acrylamide monomer and a crosslinker, the acrylamide monomer including a hydrophobic protection group, the monomer and crosslinker included in a mass ratio of monomer:crosslinker in a range of 15:1 to 1:2.

In an example of the eighth aspect, the crosslinker is a divinyl crosslinker. For example, the divinyl crosslinker can include a diacrylamide. In another example, the diacrylamide includes N,N'-(ethane-1,2-diyl)bis(N-(2-((tert-butyldimethylsilyl)oxy)ethyl)acrylamide, N,N'-(2-hydroxypropane-1,3-diyl)diacrylamide, a protected derivative thereof, or a combination thereof. The diacrylamide can, for example, include N,N'-(ethane-1,2-diyl)bis(N-(2-((tert-butyldimethylsilyl)oxy)ethyl)acrylamide, N,N'-(N-(2-((tert-butyldimethylsilyl)oxy)propane-1,3-diyl)diacrylamide, N,N'-(ethane-1,2-diyl)bis(N-(2-((triethylsilyl)oxy)ethyl)acrylamide, N,N'-(N-(2-((triethylsilyl)oxy)propane-1,3-diyl)diacrylamide, silyl-protected N-[2-(acryloylamino)-1,2-dihydroxyethyl]acrylamide such as N,N'(2,3-bis((triethylsilyl)oxy)butane-1,4-diyl)diacrylamide, or a combination thereof. In an additional example, the divinyl crosslinker includes ethyleneglycoldimethacrylate, divinylbenzene, hexamethylene bisacrylamide, trimethylolpropane trimethacrylate, or a combination thereof.

In another example of the eighth aspect or the above examples, the ratio is in a range of 10:1 to 1:1.

In a ninth aspect, a method of sequencing a polynucleotide includes providing a device including an array of wells. At least one well is operatively connected to an ISFET and includes a particle formed by the method of the above aspects. The particle is attached to a polynucleotide. The method further includes applying a solution including nucleotides of a predetermined type to the device and observing an ionic response to the applying the solution.

In a tenth aspect, a method for nucleotide incorporation includes providing a particle formed by the method of the above aspects. The particle is attached to a nucleic acid duplex including a template nucleic acid hybridized to a primer. The duplex is bound to a polymerase. The method further includes contacting the particle with one or more nucleotides and incorporating at least one nucleotide onto the end of the primer using the polymerase.

In an example of the tenth aspect, incorporating further includes generating a byproduct of nucleotide incorporation.

In another example of the tenth aspect and the above examples, the method further includes detecting the incorporating by detecting the byproduct using a field effect transistor (FET).

In an eleventh aspect, a method of forming a particle includes promoting a seed particle to form a disperse phase in an aqueous suspension, in the disperse phase, polymerizing a plurality of mer units of a hydrophilic monomer having a hydrophobic protection group, thereby forming a polymeric particle including a plurality of hydrophobic protection groups, and converting the polymeric particle to a hydrogel particle.

In a twelfth aspect, a method of forming a particle includes providing a seed particle in an aqueous suspension, the seed particle comprising a hydrophobic polymer, and includes promoting the seed particle to form a disperse phase in the aqueous suspension. The method further includes, in the disperse phase, polymerizing a plurality of mer units of a hydrophilic monomer having a hydrophobic protection group, thereby forming a polymeric particle including a hydrophilic polymer having a plurality of the hydrophobic protection groups. The polymeric particle includes the hydrophobic polymer. The method also includes cleaving the plurality of hydrophobic protection groups from the hydrophilic polymer and extracting the hydrophobic polymer from the polymeric particle to form a hydrogel particle.

In a thirteenth aspect, a particle includes a polymer formed from polymerization of hydroxyalkyl acrylamide and a diacrylamide. The diacrylamide includes a hydroxyl group. The particle absorbs at least 300 wt % water based on the weight of the polymer when exposed to water.

In an example of the thirteenth aspect, the particle absorbs at least 1000 wt % water based on the weight of the polymer when exposed to water.

In another example of the thirteenth aspect and the above examples, the particle has a particle size is not greater than 100 micrometers. For example, the particle size can be not greater than 30 micrometers, such as not greater than 1.5 micrometers.

In a further example of the thirteenth aspect and the above examples, the hydroxyalkyl acrylamide includes hydroxyethyl acrylamide.

In an additional example of the thirteenth aspect and the above examples, the hydroxyalkyl acrylamide includes N-[tris(hydroxymethyl)methyl]acrylamide (A, illustrated below), N-(hydroxymethyl)acrylamide (B, illustrated below), or a combination thereof.

In another example of the thirteenth aspect and the above examples, the diacrylamide includes N,N'-(ethane-1,2-diyl)bis(2-hydroxyl ethyl)acrylamide, N,N'-(2-hydroxypropane-1,3-diyl)diacrylamide, a protected derivative thereof, or a combination thereof. The diacrylamide can, for example, include N,N'-(ethane-1,2-diyl)bis(N-(2-((tert-butyldimethylsilyl)oxy)ethyl)acrylamide, N,N'-(N-(2-((tert-butyldimethylsilyl)oxy)propane-1,3-diyl)diacrylamide, N,N'-(ethane-1,2-diyl)bis(N-(2-((triethylsilyl)oxy)ethyl) acrylamide, N,N'-(N-(2-((triethylsilyl)oxy)propane-1,3-diyl)diacrylamide, silyl-protected N-[2-(acryloylamino)-1,2-dihydroxyethyl]acrylamide such as N,N'(2,3-bis((triethylsilyl)oxy)butane-1,4-diyl)diacrylamide, or a combination thereof.

Embodiments may be in accordance with any one of the following numbered clauses.

1. A method of forming a particle, the method comprising: in a disperse phase within an aqueous suspension, polymerizing a plurality of mer units of a hydrophilic monomer having a hydrophobic protection group, thereby forming a polymeric particle including a plurality of the hydrophobic protection groups; and converting the polymeric particle to a hydrophilic particle.

2. The method of clause 1, wherein the hydrophilic particle is a hydrogel particle.

3. The method of clause 1 or clause 2, wherein the hydrophilic monomer includes an acrylamide monomer.

4. The method of clause 1 or clause 2, wherein the hydrophilic monomer is a radically polymerizable monomer and the dispersed phase further includes a diacrylamide crosslinker having a hydrophobic protection group.

5. The method of any one of clauses 1-4, wherein converting the polymeric particle includes removing at least a portion of the plurality of the hydrophobic protection groups from the polymeric particle.

6. The method of clause 5, wherein removing at least a portion of the plurality of the hydrophobic protection groups includes acid cleaving at least a portion of the plurality of the hydrophobic protection groups from the polymeric particle.

7. The method of any one of clauses 1-6, wherein converting the polymeric particle includes removing substantially all of the plurality of hydrophobic protection groups from the polymeric particle.

8. The method of any one of clauses 1-7, further comprising promoting a seed particle in the aqueous suspension to form the dispersed phase.

9. The method of clause 8, wherein the mass ratio of protected monomer:seed particles is in a range of 150:1 to 1:1.

10. The method of clause 8, wherein the seed particle includes a seed polymer.

11. The method of clause 10, further comprising extracting the seed polymer after converting the polymeric particle.

12. The method of clause 10, wherein the seed polymer is hydrophobic.

13. The method of clause 10, wherein the seed polymer includes a styrenic polymer, an acrylic polymer, an acrylamide, another vinyl polymer, or a combination thereof.

14. The method of clause 8, wherein the seed particle has an initial particle size of not greater than 0.6 micrometers.

15. The method of clause 14, wherein the initial particle size is not greater than 0.45 micrometers.

16. The method of clause 15, wherein the initial particle size is not greater than 0.35 micrometers.

17. The method of clause 16, wherein the initial particle size is not greater than 0.15 micrometers.

18. The method of clause 8, wherein the seed particle has an initial particle size in a range of 1 micrometer to 7 micrometers.

19. The method of clause 8, wherein promoting the seed particle includes mixing a solvent and a promoting agent with the seed particle.

20. The method of clause 19, wherein the promoting agent is hydrophobic and has a water solubility of less than 0.01 g/l at 25° C.

21. The method of clause 19, wherein the promoting agent includes dioctanoyl peroxide or dioctyladipate or polystyrene with molecular weight below 20 kD.

22. The method of any one of clauses 1-21, wherein the hydrophilic monomer includes an acrylamide.

23. The method of any one of clauses 4-22, wherein the radically polymerizable monomer is a vinyl-based monomer.

24. The method of clause 23, wherein the vinyl-based monomer includes an acrylate, an acrylamide, a vinyl alcohol, a vinyl acetate, acrylamido-methyl-propanesulfonic acid, or a combination thereof.

25. The method of clause 24, wherein the vinyl-based monomer is an acrylamide.

26. The method of any one of clauses 1-25, wherein the hydrophobic protection group includes a hydroxyl protection group.

27. The method of any one of clauses 1-25, wherein the hydrophobic protection group includes an amine protection group.

28. The method of any one of clauses 1-27, wherein the hydrophobic protection group includes an organometallic moiety.

29. The method of clause 28, wherein the organometallic moiety forms a silyl ether functional group.

30. The method of clause 29, wherein the silyl ether function group is derived from tert-butyldimethylsilane ether, trimethylsilyl ether, triethylsilyl ether, diphenyl methyl silyl ether, or a combination thereof.

31. The method of any one of clauses 1-30, wherein polymerizing the plurality of mer units further includes mixing a crosslinker with the hydrophilic monomer having a hydrophobic protection group.

32. The method of clause 31, wherein mixing the crosslinker includes mixing the crosslinker at a mass ratio of hydrophilic monomer:crosslinker in a range of 15:1 to 1:2.

33. The method of clause 32, wherein the range is 10:1 to 1:1.

34. The method of clause 31, wherein the crosslinker is a low water solubility crosslinker and has a water solubility of less than 10 g/l at 25° C.

35. The method of clause 31, wherein the crosslinker is a divinyl crosslinker.

36. The method of clause 35, wherein the divinyl crosslinker includes a diacrylamide.

37. The method of clause 4 or clause 36, wherein the diacrylamide includes N,N'-(ethane-1,2-diyl)bis(N-(2-((tert-butyldimethylsilyl)oxy)ethyl)acrylamide, N,N'-(2-hydroxypropane-1,3-diyl)diacrylamide, a protected derivative thereof, or a combination thereof.

38. The method of clause 4 or clause 37, wherein the diacrylamide includes N,N'-(ethane-1,2-diyl)bis(N-(2-((tert-butyldimethylsilyl)oxy)ethyl)acrylamide, N,N'-(N-(2-((tert-butyldimethylsilyl)oxy)propane-1,3-diyl)diacrylamide, N,N'-(ethane-1,2-diyl)bis(N-(2-((triethylsilyl)oxy)ethyl) acrylamide, N,N'-(N-(2-((triethylsilyl)oxy)propane-1,3-diyl)diacrylamide, silyl-protected N-[2-(acryloylamino)-1,2-dihydroxyethyl]acrylamide such as N,N'(2,3-bis ((triethylsilyl)oxy)butane-1,4-diyl)diacrylamide, or a combination thereof.

39. The method of clause 35, wherein the divinyl crosslinker includes ethyleneglycoldimethacrylate, divinylbenzene, hexamethylene bisacrylamide, trimethylolpropane trimethacrylate, or a combination thereof.

40. The method of any one of clauses 1-39, wherein polymerizing the plurality of mer units includes mixing a porogen with the hydrophilic monomer having a hydrophobic protection group.

41. The method of clause 40, wherein the porogen is an aromatic porogen.

42. The method of clause 41, wherein the aromatic porogen includes toluene, xylene, mesitylene, phenylenethyl acetate or ethylbenzoate.

43. The method of any one of clauses 1-42, further comprising activating the hydrophilic particle or the hydrogel particle.

44. The method of clause 43, wherein converting includes providing one or more hydroxyl groups on the hydrogel particle and wherein activating includes converting at least one of the one or more hydroxyl groups to alkyl or aryl sulfonic esters.

45. The method of clause 43, wherein converting includes providing one or more hydroxyl groups on the hydrogel particle and wherein activating includes replacing at least one of the one or more hydroxyl groups with an azide functional moiety.

46. The method of clause 43, wherein converting includes providing one or more amine groups on the hydrogel particle and wherein activating includes reacting at least one of the one or more amine groups with bis-succinimidyl C2-C12 alkyl ester.

47. The method of clause 43, further comprising binding an oligonucleotide to the activated hydrogel polymer.

48. The method of clause 47, wherein binding includes nucleophilic substitution and the oligonucleotide is a nucleophile-terminated oligonucleotide.

49. The method of clause 48, wherein a nucleophile of the nucleophile-terminated oligonucleotide is an amine group.

50. The method of clause 48, wherein a nucleophile of the nucleophile-terminated oligonucleotide is a thiol group.

51. The method of clause 47, further comprising hybridizing a polynucleotide to the oligonucleotide.

52. The method of clause 51, further comprising amplifying the polynucleotide into a plurality of polynucleotides and attaching at least a portion of the plurality of polynucleotides to the hydrogel particle, thereby generating a hydrogel particle including a plurality of attached polynucleotides.

53. The method of clause 51, further comprising amplifying the polynucleotide into a plurality of complementary polynucleotides by extending the oligonucleotide, thereby generating a hydrogel particle including a plurality of attached polynucleotides.

54. The method of any one of clauses 1-53, wherein the hydrogel particle is one of a plurality of similarly formed hydrogel particles having an average particle size of not greater than 2 micrometer in water.

55. The method of clause 54, wherein the average particle size is not greater than 1 micrometer.

56. The method of clause 55, wherein the average particle size is not greater than 0.8 micrometers.

57. The method of clause 56, wherein the average particle size is not greater than 0.5 micrometers.

58. The method of any one of clauses 1-44, wherein the hydrogel particle is one of a plurality of similarly formed hydrogel particles having an average particle size in a range of 5 micrometers to 100 micrometers in water.

59. The method of any one of clauses 1-58, wherein the hydrogel particle is one of a plurality of similarly formed hydrogel particles that are substantially uniform in size.

60. The method of any one of clauses 1-59, wherein the hydrogel particle is one of a plurality of similarly formed hydrogel particles having a coefficient of variance of not greater than 5.0%.

61. The method of clause 60, wherein the coefficient of variance of not greater than 3.5%.

62. A method of forming a particle, the method comprising: polymerizing a plurality of mer units of a hydrophilic monomer having a hydrophobic protection group, thereby forming a polymeric particle including a plurality of the hydrophobic protection groups; removing at least a portion of plurality of the hydrophobic protection groups from the polymeric particle to form a hydrophilic particle; and binding an oligonucleotide to the hydrophilic particle.

63. The method of clause 62, wherein removing at least a portion of the plurality of the hydrophobic protection groups includes acid cleaving at least a portion of the plurality of the hydrophobic protection groups from the polymeric particle.

64. The method of clause 62 or 63, wherein the hydrophilic monomer includes an acrylamide.

65. The method of any one of clauses 62-64, wherein the hydrophobic protection group includes a hydroxyl protection group.

66. The method of any one of clauses 62-65, wherein the hydrophobic protection group includes an organometallic moiety.

67. The method of clause 66, wherein the organometallic moiety forms a silyl ether functional group.

68. The method of any one of clauses 62-67, wherein polymerizing the plurality of mer units further includes mixing a crosslinker with the hydrophilic monomer having a hydrophobic protection group.

69. The method of clause 68, wherein the crosslinker is a divinyl crosslinker.

70. The method of clause 69, wherein the divinyl crosslinker includes a diacrylamide.

71. The method of any one of clauses 62-70, further comprising activating the hydrogel particle prior to binding the oligonucleotide.

72. The method of clause 71, wherein removing includes providing one or more hydroxyl groups on the hydrophilic particle and wherein activating includes converting at least one of the one or more hydroxyl groups to a sulfonate ester group.

73. The method of clause 71, wherein removing includes providing one or more hydroxyl groups on the hydrophilic particle and wherein activating includes replacing at least one of the one or more hydroxyl groups with an azide functional moiety.

74. The method of clause 71, wherein binding includes binding the oligonucleotide to the activated hydrogel polymer.

75. The method of clause 74, wherein binding includes nucleophilic substitution and the oligonucleotide is a nucleophile-terminated oligonucleotide.

76. The method of clause 75, wherein a nucleophile of the nucleophile-terminated oligonucleotide is an amine group.

77. The method of clause 75, wherein a nucleophile of the nucleophile-terminated oligonucleotide is a thiol group.

78. The method of any one of clauses 62-77, further comprising hybridizing a polynucleotide to the oligonucleotide.

79. The method of clause 78, further comprising amplifying the polynucleotide into a plurality of polynucleotides and attaching at least a portion of the plurality of polynucleotides to the hydrogel particle, thereby generating a hydrogel particle including a plurality of attached polynucleotides.

80. The method of clause 78, further comprising amplifying the polynucleotide into a plurality of complementary polynucleotides by extending the oligonucleotide, thereby generating a hydrogel particle including a plurality of attached polynucleotides.

81. A plurality of particles comprising at least 100,000 particles, at least one particle of the plurality of particles comprising a hydrogel, the plurality of particles having an average particle size of not greater than 100 micrometers and a coefficient of variance of not greater than 5%.

82. The plurality of particles of clause 81, wherein each of the at least 100,000 particles comprises the hydrogel.

83. The plurality of particles of clause 81 or 82, wherein the coefficient of variance is not greater than 4.5%.

84. The plurality of particles of clause 83, wherein the coefficient of variance is not greater than 4.0%.

85. The plurality of particles of clause 84, wherein the coefficient of variance is not greater than 3.5%.

86. The plurality of particles of clause 85, wherein the coefficient of variance is not greater than 3.0%.

87. The plurality of particles of any one of clauses 81-86, wherein the average size is not greater than 30 micrometers.

88. The plurality of particles of clause 87, wherein the average size is not greater than 1.5 micrometers.

89. The plurality of particles of clause 88, wherein the average size is not greater than 1.1 micrometers.

90. The plurality of particles of clause 89, wherein the average size is not greater than 0.6 micrometers.

91. The plurality of particles of clause 90, wherein the average size is not greater than 0.5 micrometers.

92. The plurality of particles of any one of clauses 81-91, wherein the hydrogel includes an acrylamide polymer.

93. The plurality of particles of any one of clauses 81-92, wherein the particles of the plurality of particles have an average porosity of at least 60%.

94. A system comprising: an array of wells, at least one well of the array of wells being operatively connected with an ISFET sensor; and a plurality of hydrogel particles having a coefficient of variance of not greater than 5%, at least one of the hydrogel particles of the plurality of hydrogel particles being disposed in a well of the array of wells.

95. A plurality of particles formed by the method comprising: in a disperse phase within an aqueous suspension, polymerizing a plurality of mer units of a hydrophilic monomer having a hydrophobic protection group, thereby forming a polymeric particle including a plurality of the hydrophobic protection groups; and converting the polymeric particle to a hydrogel particle.

96. The plurality of particles of clause 95, wherein the plurality of particles has a coefficient of variance of not greater than 5.0%.

97. The plurality of particles of clause 96, wherein the coefficient of variance is not greater than 4.0%.

98. The plurality of particles of clause 97, wherein the coefficient of variance is not greater than 3.5%.

99. The plurality of particles of clause 98, wherein the coefficient of variance is not greater than 3.0%.

100. The plurality of particles of any one of clauses 95-99, wherein the plurality of particles have an average size of not greater than 100 micrometers.

101. The plurality of particles of clause 100, wherein the average size is not greater than 30 micrometers.

102. The plurality of particles of clause 101, wherein the average size is not greater than 5 micrometers.

103. The plurality of particles of clause 102, wherein the average size is not greater than 1.5 micrometers.

104. The plurality of particles of clause 103, wherein the average size is not greater than 0.8 micrometers.

105. The plurality of particles of any one of clauses 95-104, wherein the hydrophilic monomer includes an acrylamide monomer.

106. The plurality of particles of any one of clauses 95-105, wherein the particles of the plurality of particles have an average porosity of at least 60%.

107. A composition comprising an aqueous mixture of an acrylamide monomer and a crosslinker, the acrylamide monomer including a hydrophobic protection group, the monomer and crosslinker included in a mass ratio of monomer:crosslinker in a range of 15:1 to 1:2.

108. The composition of clause 107, wherein the crosslinker is a divinyl crosslinker.

109. The composition of clause 108, wherein the divinyl crosslinker includes a diacrylamide.

110. The composition of clause 109, wherein the diacrylamide includes N.N'-(ethane-1,2-diyl)bis(N-(2-((tert-butyldimethylsilyl)oxy)ethyl)acrylamide, N,N'-(2-hydroxypropane-1,3-diyl)diacrylamide, a protected derivative thereof, or a combination thereof.

111. The composition of clause 110, wherein the diacrylamide includes N,N'-(ethane-1,2-diyl)bis(N-(2-((tert-butyldimethylsilyl)oxy)ethyl)acrylamide, N,N'-(N-(2-((tert-butyldimethylsilyl)oxy)propane-1,3-diyl)diacrylamide, N,N'-(ethane-1,2-diyl)bis(N-(2-((triethylsilyl)oxy)ethyl) acrylamide, N,N'-(N-(2-((triethylsilyl)oxy)propane-1,3-diyl)diacrylamide, silyl-protected N-[2-(acryloylamino)-1,2-dihydroxyethyl]acrylamide such as N,N'(2,3-bis ((triethylsilyl)oxy)butane-1,4-diyl)diacrylamide, or a combination thereof.

112. The composition of clause 108, wherein the divinyl crosslinker includes ethyleneglycoldimethacrylate, divinylbenzene, hexamethylene bisacrylamide, trimethylolpropane trimethacrylate, or a combination thereof.

113. The composition of any one of clauses 107-112, wherein the ratio is in a range of 10:1 to 1:1.

114. A method of sequencing a polynucleotide, the method comprising: providing a device including an array of wells, at least one well being operatively connected to an ISFET and including a particle formed by the method of any one of clauses 1-80, the particle being attached to a polynucleotide, applying a solution including nucleotides of a predetermined type to the device; and observing an ionic response to the applying the solution.

115. A method for nucleotide incorporation, comprising: providing a particle formed by the method any one of clauses 1-80, the particle being attached to a nucleic acid duplex including a template nucleic acid hybridized to a primer, the duplex being bound to a polymerase; contacting the particle with one or more nucleotides; and incorporating at least one nucleotide onto the end of the primer using the polymerase.

116. The method of clause 115, wherein the incorporating further includes generating a byproduct of nucleotide incorporation.

117. The method of clause 115 or 116, further including detecting the incorporating by detecting the byproduct using a field effect transistor (FET).

118. A method of forming a particle, the method comprising: promoting a seed particle to form a disperse phase in an aqueous suspension; in the disperse phase, polymerizing a plurality of mer units of a hydrophilic monomer having a hydrophobic protection group, thereby forming a polymeric particle including a plurality of hydrophobic protection groups; and converting the polymeric particle to a hydrogel particle.

119. A method of forming a particle, the method comprising: providing a seed particle in an aqueous suspension, the seed particle comprising a hydrophobic polymer; promoting the seed particle to form a disperse phase in the aqueous suspension; in the disperse phase, polymerizing a plurality of mer units of a hydrophilic monomer having a hydrophobic protection group, thereby forming a polymeric particle including a hydrophilic polymer having a plurality of the hydrophobic protection groups, the polymeric particle including the hydrophobic polymer; cleaving the plurality of hydrophobic protection groups from the hydrophilic polymer; and extracting the hydrophobic polymer from the polymeric particle to form a hydrogel particle.

120. A population of particles having a coefficient of variance of not greater than 5% and comprising a polymer formed from polymerization of hydroxyalkyl acrylamide and a diacrylamide, the diacrylamide including a hydroxyl group, wherein the particle absorbs at least 300 wt % water based on the weight of the polymer when exposed to water.

121. The particle of clause 120, wherein the particle absorbs at least 1000 wt % water based on the weight of the polymer when exposed to water.

122. The particle of clause 120 or 121, wherein the particle has a particle size of not greater than 100 micrometers.

123. The particle of clause 122, wherein the particle size is not greater than 30 micrometers.

124. The particle of clause 123, wherein the particle size is not greater than 1.5 micrometers.

125. The particle of any one of clauses 120-124, wherein the hydroxyalkyl acrylamide includes hydroxyethyl acrylamide.

126. The particle of any one of clauses 120-125, wherein the hydroxyalkyl acrylamide includes N-[tris(hydroxymethyl)methyl)acrylamide, N-(hydroxymethyl)acrylamide, or a combination thereof.

127. The particle of any one of clauses 120-126, wherein the diacrylamide includes N,N'-(ethane-1,2-diyl)bis(2-hydroxyl ethyl)acrylamide, N,N'-(2-hydroxypropane-1,3-diyl)diacrylamide, a protected derivative thereof, or a combination thereof.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A particle comprising a polymer formed from polymerization of hydroxyalkyl acrylamide and a diacrylamide, the diacrylamide including a hydroxyl group, wherein the particle absorbs at least 300 wt % water based on the weight of the polymer when exposed to water.

2. The particle of claim 1, wherein the particle absorbs at least 1000 wt % water based on the weight of the polymer when exposed to water.

3. The particle of claim 1, wherein the particle has a particle size of not greater than 100 micrometers.

4. The particle of claim 3, wherein the particle size is not greater than 30 micrometers.

5. The particle of claim 4, wherein the particle size is not greater than 1.5 micrometers.

6. The particle of claim 1, wherein the hydroxyalkyl acrylamide includes hydroxyethyl acrylamide.

7. The particle of claim 1, wherein the hydroxyalkyl acrylamide includes N-[tris(hydroxymethyl)methyl)acrylamide, N-(hydroxymethyl)acrylamide, or a combination thereof.

8. The particle of claim 1, wherein the diacrylamide includes N,N'-(ethane-1,2-diyl)bis(2-hydroxyl ethyl)acrylamide, N,N'-(2-hydroxypropane-1,3-diyl)diacrylamide, a protected derivative thereof, or a combination thereof.

* * * * *